US012616405B2

(12) United States Patent
     Apperson et al.

(10) Patent No.: US 12,616,405 B2
(45) Date of Patent: May 5, 2026

(54) PROVIDING A LIVE-LEAD VIEW

(71) Applicant: Physio-Control, Inc., Redmond, WA (US)

(72) Inventors: Ryan W. Apperson, Bothell, WA (US); Rick Palm, Seattle, WA (US); David J. Linville, Woodinville, WA (US); Michelle Liu, Sammamish, WA (US); Tyson G. Taylor, Bothell, WA (US); Ronald E. Stickney, Edmonds, WA (US)

(73) Assignee: Physio-Control, Inc., Redmond, WA (US)

( * ) Notice: Subject to any disclaimer, the term of this patent is extended or adjusted under 35 U.S.C. 154(b) by 1213 days.

(21) Appl. No.: 17/522,611

(22) Filed: Nov. 9, 2021

(65) Prior Publication Data

US 2022/0160282 A1 May 26, 2022

Related U.S. Application Data

(60) Provisional application No. 63/118,251, filed on Nov. 25, 2020.

(51) Int. Cl.
     *A61B 5/271* (2021.01)
     *A61B 5/00* (2006.01)
     *A61B 5/0245* (2006.01)
     *A61B 5/0255* (2006.01)
     *A61B 5/28* (2021.01)
     *A61B 5/339* (2021.01)

(52) U.S. Cl.
     CPC .............. *A61B 5/271* (2021.01); *A61B 5/28* (2021.01); *A61B 5/339* (2021.01); *A61B 5/686* (2013.01); *A61B 5/7203* (2013.01); *A61B 5/7246* (2013.01)

(58) Field of Classification Search
     CPC ........... A61B 5/271; A61B 5/28; A61B 5/339; A61B 5/686; A61B 5/7203; A61B 5/7246; A61B 5/7221; A61B 5/0255; A61B 5/7435; A61B 5/0245
     See application file for complete search history.

(56) References Cited

U.S. PATENT DOCUMENTS

| | | | |
|---|---|---|---|
| 6,516,218 B1 * | 2/2003 | Cheng ..................... | A61B 5/086 |
| | | | 600/509 |
| 2009/0167286 A1 | 7/2009 | Naylor et al. | |

(Continued)

OTHER PUBLICATIONS

Extended European Search Report for related European Patent Application No. 21210490.5 mailed Apr. 29, 2022.

(Continued)

*Primary Examiner* — Justin Xu

(74) *Attorney, Agent, or Firm* — McDonnell Boehnen Hulbert & Berghoff LLP

(57) ABSTRACT

An example method is performed by an electrocardiogram (ECG) device and includes determining a number of lead wires of an ECG cable assembly that is attached to the ECG device. The method also includes receiving ECG signals using electrodes of the ECG cable assembly. Further, the method includes using the number of lead wires as a basis for selecting a live-lead view from among a first live-lead view and a second live-lead view. Still further, the method includes displaying a representation of the ECG signals in the selected live-lead view in accordance with the selection.

17 Claims, 16 Drawing Sheets

(56)        References Cited

U.S. PATENT DOCUMENTS

| | | |
|---|---|---|
| 2013/0331721 A1 | 12/2013 | Battaglia |
| 2015/0141862 A1* | 5/2015 | Montambeau ......... A61B 5/743 |
| | | 600/523 |
| 2016/0066805 A1 | 3/2016 | Scherf et al. |
| 2016/0174896 A1* | 6/2016 | Kn ....................... A61N 1/3937 |
| | | 600/510 |
| 2017/0086696 A1* | 3/2017 | Chen ...................... A61B 5/349 |
| 2017/0095217 A1* | 4/2017 | Hubert ................... A61B 5/742 |

OTHER PUBLICATIONS

Communication Pursuant to Article 94(3) EPC issued by the European Patent Office in application EP 21 210 490.5 dated Mar. 24, 2025.

* cited by examiner

1600

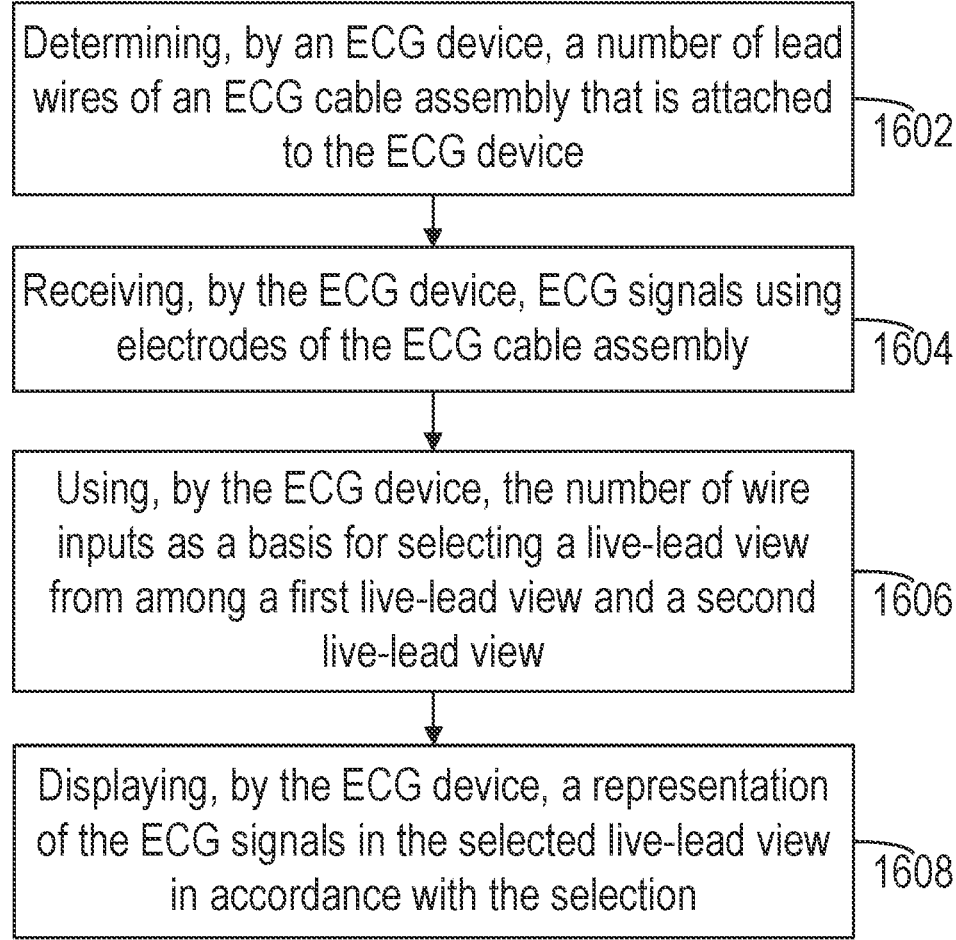

Determining, by an ECG device, a number of lead wires of an ECG cable assembly that is attached to the ECG device — 1602

Receiving, by the ECG device, ECG signals using electrodes of the ECG cable assembly — 1604

Using, by the ECG device, the number of wire inputs as a basis for selecting a live-lead view from among a first live-lead view and a second live-lead view — 1606

Displaying, by the ECG device, a representation of the ECG signals in the selected live-lead view in accordance with the selection — 1608

FIG. 16

PROVIDING A LIVE-LEAD VIEW

CROSS-REFERENCE TO RELATED APPLICATIONS

The present application claims priority to U.S. provisional application No. 63/118,251, filed on Nov. 25, 2020, the entire contents of which are herein incorporated by reference.

BACKGROUND

An electrocardiogram (ECG) device measures electrical activity of a patient's heart using electrodes placed on the patient's skin. In operation, the ECG device may output one or more graphs of voltage over time, referred to as an ECG. A medical professional can evaluate an ECG to diagnose a patient's condition.

An ECG lead is a view of electrical activity of a heart from a particular angle. Some ECG devices, referred to as single-lead devices, provide just a single ECG lead using two electrodes. Other ECG devices provide multiple ECG leads. For instance, a 12-lead ECG provides twelve ECG leads using ten electrodes, while a 15-lead ECG provides fifteen ECG leads using thirteen electrodes. 12-lead and 15-lead ECG devices are used on patients of all ages to identify and diagnose cardiac abnormalities. In addition, 12-lead and 15-lead ECG devices are useful in the early detection of patients with acute ST-elevation myocardial infarction (STEMI).

SUMMARY

Within examples described herein, systems and methods are described that allow users of an ECG device to observe and improve ECG quality before generating an ECG report.

The features, functions, and advantages that have been discussed can be achieved independently in various examples or may be combined in yet other examples. Further details of the examples can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

FIG. 16 shows a flowchart of an example of a method, according to an example implementation.

DETAILED DESCRIPTION

Figure 1:
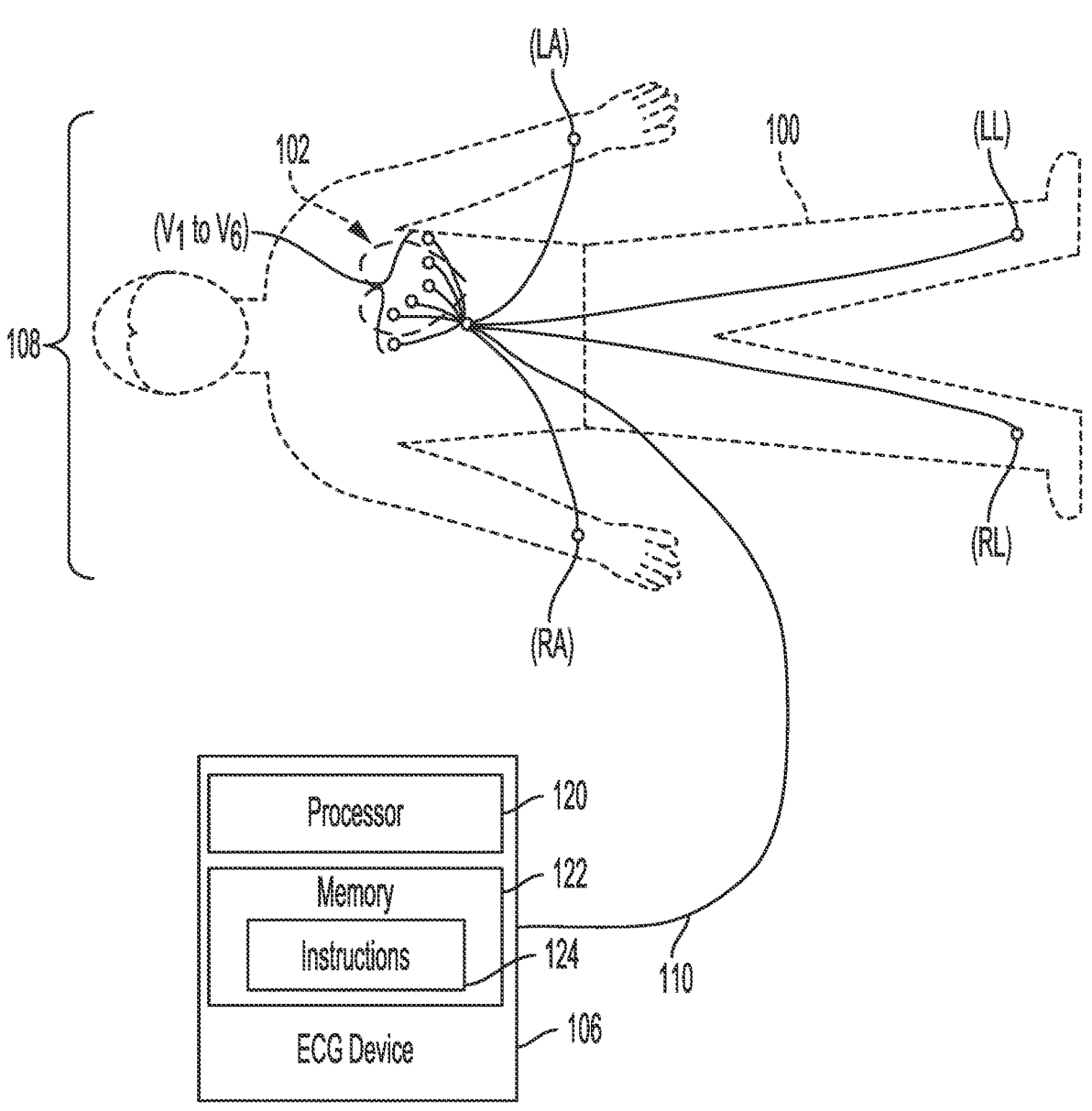
FIG. 1 illustrates an example defibrillation scene, according to an example implementation.

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

Currently, to obtain an ECG report, a user of an ECG device first applies electrodes to a patient. The user then presses a button or otherwise issues a command that causes the ECG device to acquire ECG signals for an analysis time period (e.g., ten seconds), analyze the ECG signals, generate a report, and print out and/or save the ECG report. If, however, any of the ECG signals are noisy, a portion of the ECG report might not be usable by a medical professional to assess the condition of a patient's heart. Accordingly, the user may attempt to remedy the issue by reapplying or adjusting one of the electrodes, and repeat the procedure, hoping that the corrective action was successful. This guess-and-check approach for improving the quality of an ECG report is inefficient, especially for a patient that is experiencing a heart problem and is need of urgent, life-saving treatment. Moreover, given this urgency, this guess-and-check approach increases the risk of errors by medical personnel in obtaining a satisfactory ECG result.

Example methods and devices described herein allow users of an ECG device to observe and improve ECG quality before generating an ECG report. By way of example, prior to analyzing ECG signals and generating an ECG report, an ECG device can provide a live-lead view of multiple ECG leads. The live-lead view can include waveform representations of ECG leads, and a user of the ECG device can use the live-lead view to assess the quality of electrode connections. For instance, if a waveform representation of a particular ECG lead is indicative of poor contact between an electrode and the patient, the user of the ECG device can remove and reapply or replace the electrode, or encourage the patient to hold still. In near real-time (e.g., within a second or two), the user can determine whether the corrective action improved the quality of the particular ECG lead by observing the ECG lead on the live-lead view. After correcting the issue, the user of the ECG device can then cause the ECG device to acquire and analyze ECG signals, and generate an ECG report.

In addition, the ECG device can automatically adjust the live-lead view based on whether the user is attempting to obtain a 12-lead ECG or a 15-lead ECG. For instance, the ECG device can determine a number of lead wires of an ECG cable assembly attached to the ECG device, and use the number of lead wires as a basis for selecting between a live twelve-lead view and a live fifteen-lead view.

Further details and features of these methods and systems are described hereinafter with reference to the figures.

Referring now to the figures, FIG. 1 illustrates a diagram of a defibrillation scene showing use of an external defibrillator to save the life of a person, according to an example implementation. As shown in FIG. 1, a person 100 is lying on their back. The person 100 could be a patient in a hospital, a clinic, a doctor's office, an ambulance, a public location, a home, or just about anywhere that emergency medical services might be called. The person 100 may be experiencing a condition in their heart 102, or they may be experiencing a different medical problem such as stroke, or they may be getting an ECG for a medical checkup. An ECG device 106 has been brought close to the person 100. The ECG device 106 receives voltage signals from multiple electrodes through lead wires 110, and the ECG device 106 combines the voltage signals in various ways to form multiple ECG leads.

In FIG. 1, the multiple electrodes include ten electrodes. The ten electrodes include four limb electrodes: RA (right arm), LA (left arm), RL (right leg), and LL (left leg); and six precordial (chest) electrodes, which are labeled $V_1$ to $V_6$ (precordial electrodes). Each of the ten electrodes may be coupled to the person 100 using adhesive and are typically about two inches in diameter, for example.

An ECG lead is a view of electrical activity of the heart 102 from a particular angle. In FIG. 1, a 12-lead ECG system is shown in which the ten electrodes provide twelve perspectives of activity of the heart 102 using different angles through two electrical planes, namely, frontal and horizontal planes. The twelve ECG leads include: three bipolar limb leads (I, II, and III), three augmented limb leads (augmented vector right (aVR), augmented vector left (aVL), and augmented vector foot (aVF)), and six chest leads also called precordial or V leads, (V1, V2, V3 V4, V5, and V6). In this document, precordial electrodes and lead wires will use subscripted numbers in their labels (e.g., $V_1$) and precordial leads will not (e.g., V1).

By using three limb electrodes (RA, LA, and LL), six frontal leads can be derived that provide information about the vertical plane of the heart 102. The six frontal leads can be labeled and derived using the lead equations shown below. The RL electrode is the neutral electrode and is not used in any lead equations.

$$I = LA - RA \qquad \text{Equation (1)}$$

$$II = LL - RA \qquad \text{Equation (2)}$$

$$III = LL - LA \qquad \text{Equation (3)}$$

$$aVR = RA - (LA + LL)/2 \qquad \text{Equation(4)}$$

$$aVL = LA - (RA + LL)/2 \qquad \text{Equation (5)}$$

$$aVF = LL - (LA + RA)/2 \qquad \text{Equation (6)}$$

Limb lead I is taken between a negative electrode placed on the right arm and a positive electrode placed on the left arm; limb lead II between a negative electrode placed on the right arm and a positive electrode placed on the left leg; and so forth. These and the other electrode pairings to form the 12-lead ECG orientations are well known in electrocardiography.

Then, by using the six chest electrodes, six precordial leads can be derived that provide information about the horizontal plane of the heart 102 using the lead equations shown below.

$$V1 = V_1 - (LA + RA + LL)/3 \qquad \text{Equation (7)}$$

$$V2 = V_2 - (LA + RA + LL)/3 \qquad \text{Equation (8)}$$

$$V3 = V_3 - (LA + RA + LL)/3 \qquad \text{Equation (9)}$$

$$V4 = V_4 - (LA + RA + LL)/3 \qquad \text{Equation (10)}$$

$$V5 = V_5 - (LA + RA + LL)/3 \qquad \text{Equation (11)}$$

$$V6 = V_6 - (LA + RA + LL)/3 \qquad \text{Equation (12)}$$

The ECG device 106 may be an electrocardiograph that takes a "snapshot" of the 12-lead ECG and is used to detect various cardiac abnormalities. In other examples, the ECG device 106 may be used to continuously or periodically assess the heart rhythm and heart rate. Thus, the ECG device 106 can further include an ECG monitor or other components, such as a processor 120 and memory 122, and optionally a display (not shown). In further examples, the ECG device 106 could be a combined monitor and electrocardiograph. Furthermore, the combined monitor and electrocardiograph could also contain a defibrillator. Thus, in other examples, the ECG device 106 may include an external defibrillator (not shown).

By way of example, the ECG device 106 can be a monitor defibrillator. Monitor defibrillators are intended to be used by trained medical professionals, such as doctors, nurses, paramedics, emergency medical technicians, etc. As the name suggests, a monitor defibrillator is a combination of a monitor and a defibrillator. As a defibrillator, a monitor defibrillator can be one of different varieties, or even versatile enough to be able to switch among different modes that individually correspond to the varieties. One variety is that of an automated defibrillator, which can determine whether a shock is needed and, if so, charge to a predetermined energy level and instruct the user to deliver the shock. Another variety is that of a manual defibrillator, where the user determines the need and controls delivery of the shock. As a patient monitor, the monitor defibrillator has features additional to what is needed for operation as a defibrillator. These features can be for monitoring physiological indicators of a patient in an emergency scenario, for instance.

In general, the ECG device 106 may take the form of a computing device with multiple storage partitions and processors for performing functions described herein.

The processor 120 is configured to execute an instance for acquiring the ECG of the person 100. The processor 120 may be implemented in any number of ways. Such ways include, by way of example and not of limitation, digital and/or analog processors such as microprocessors and digital-signal processors (DSPs); controllers such as microcontrollers, software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on. Thus, the processor 120 may be general-purpose processors or special purpose processors (e.g., digital signal processors, application specific integrated circuits, etc.). The processor 120 may receive inputs from the multi-lead ECG system 108, and process the inputs to generate outputs that are stored in the memory 122.

The memory 122 may be implemented in any number of ways. Such ways include, by way of example and not of limitation, nonvolatile memories (NVM), read-only memories (ROM), random access memories (RAM), any combination of these, etc. In one example, the memory 122 is a non-transitory computer-readable medium having stored therein a plurality of executable instructions 124, which are executable by the processor 120 or other processors that may be included in the ECG device 106. The memory is considered non-transitory computer readable media. In some examples, the memory 122 can be implemented using a single physical device (e.g., one optical, magnetic, organic or other memory or disc storage unit), while in other examples, the memory 122 can be implemented using two or more physical devices.

The processor 120 can be configured to execute the instructions 124 (e.g., computer-readable program instructions) that are stored in the memory 122 and are executable to provide the functionality described herein. Within one example, in operation, when the instructions 124 are executed by the processor 120, the processor 120 is caused to perform functions including determining a number of lead wires of an ECG cable assembly, receiving ECG signals using electrodes of the ECG cable assembly, using the number of lead wires as a basis for selecting a live-lead view from among a first live-lead view and a second live-lead view, and displaying a representation of the ECG signals in the selected live-lead view in accordance with the selection. Details of these functions are described below.

Figure 2:
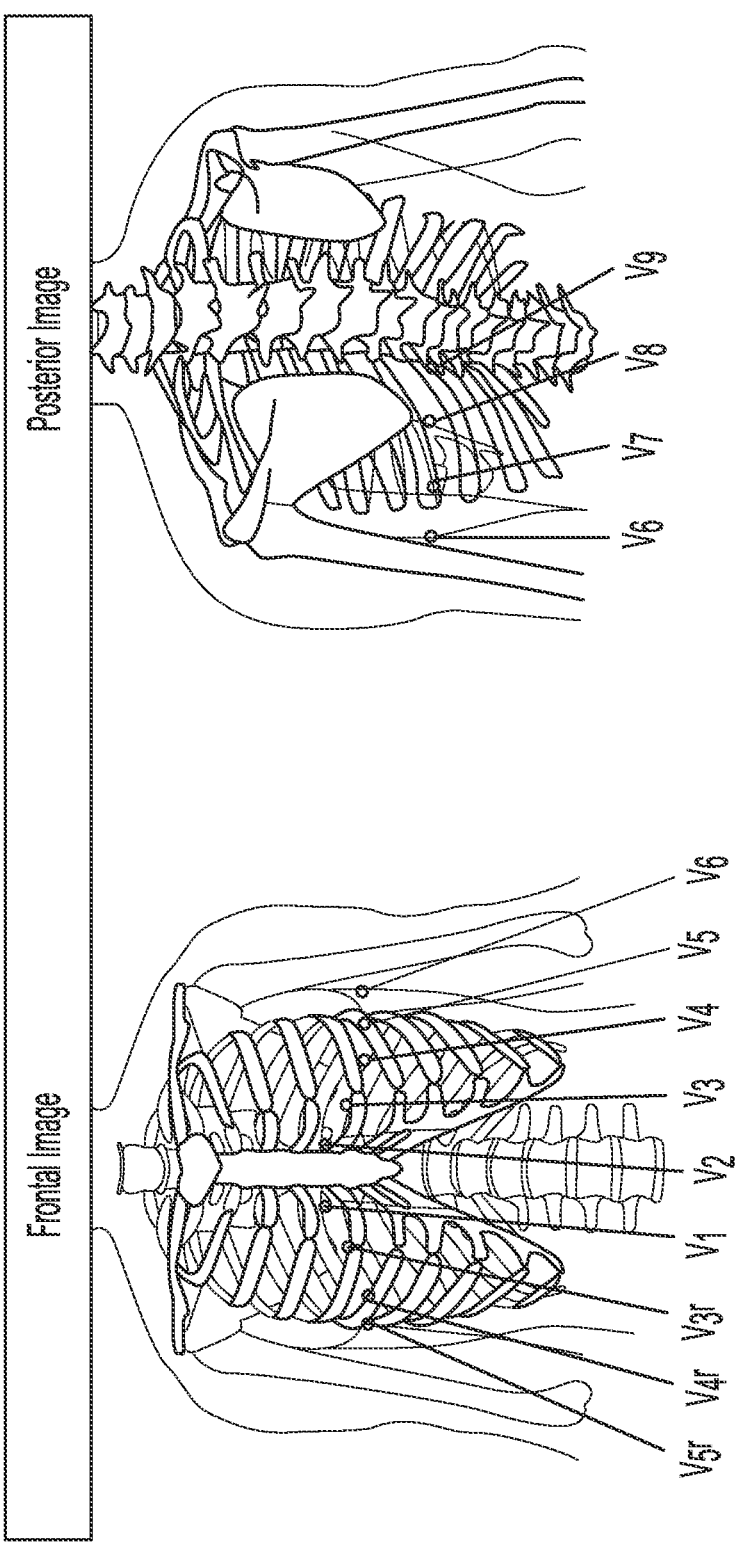
FIG. 2 illustrates example electrode sites, according to an example implementation.

To obtain a 15-lead ECG, three additional electrodes are placed either on the right side of a chest of the patient, on the left side of the back of the patient. FIG. 2 illustrates additional electrode sites, according to an example implementation. As shown in FIG. 2, additional electrode sites $V_3r$ through $V_5r$ are available on the front, right side of a patient's chest. Further, electrode sites $V_7$ through $V_9$ are available on the left, back side of a patient's chest. Equations for those V leads are like the equations for the standard V leads, in general form:

$$Vn = V_n - (LA + RA + LL)/3 \qquad \text{Equation (13)}$$

In some examples, when using a 12-lead ECG, some of the precordial lead wires can be attached to different electrode sites than those indicated in FIG. 1. For instance, the $V_3$, $V_4$, and $V_5$ electrodes can be moved to the $V_3r$, $V_4R$, and $V_5r$ electrode sites, respectively, on the right side of the patient's chest. Alternatively, the $V_4$, $V_5$, and $V_6$ electrodes can be moved to the $V_7$, $V_8$, and $V_9$ electrode sites, respectively, on the back side of the patient's chest. This can allow a medical professional to obtain different perspectives of the electrical activity of the patient's heart.

Figure 3:
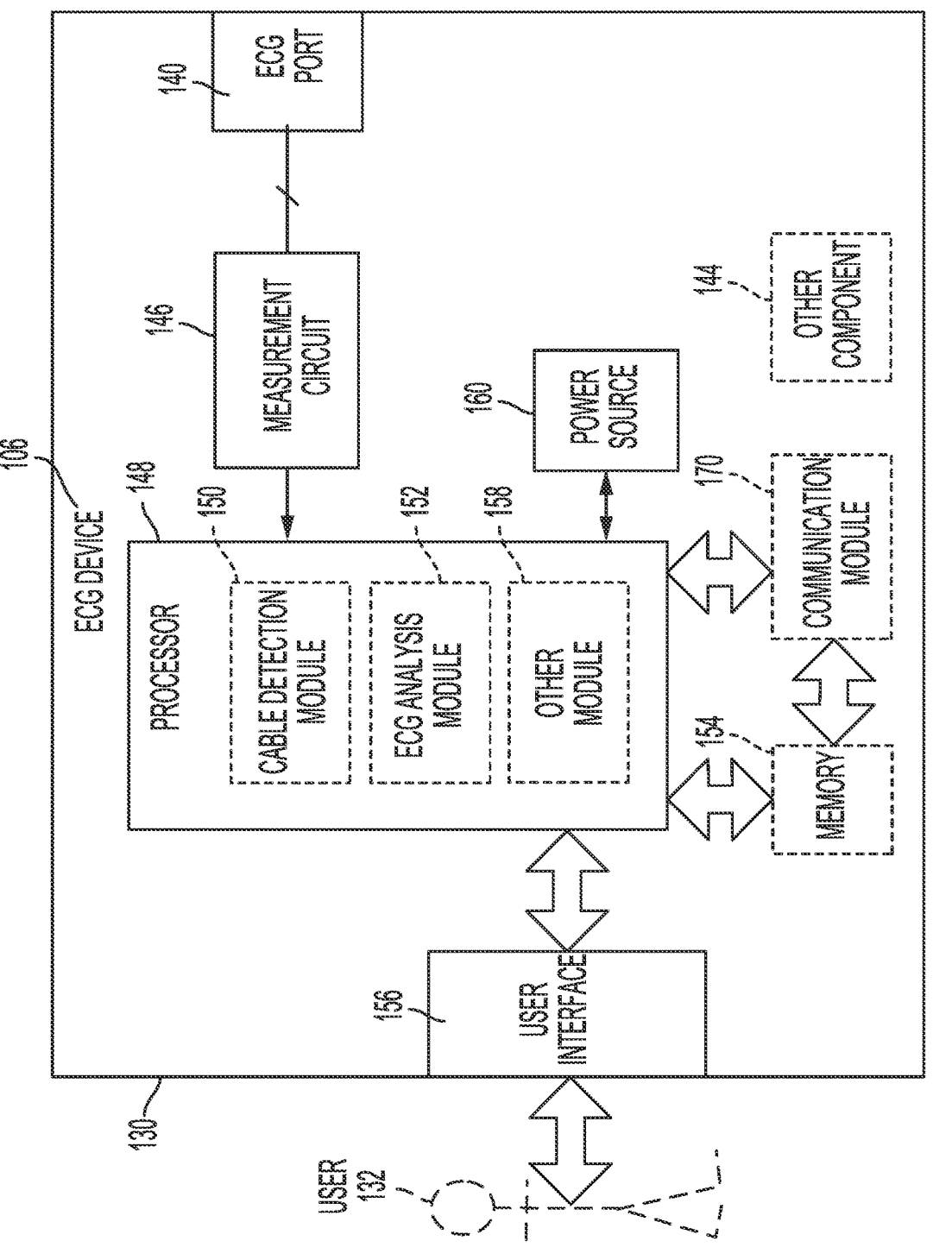
FIG. 3 is a diagram showing example components of an ECG device, according to an example implementation.

FIG. 3 is a diagram showing example components of the ECG device 106, according to an example implementation. These components of FIG. 3 can be provided in a housing 130, which is also known as a casing.

The ECG device 106 is intended for use by a user 132, who would be the care provider. The ECG device 106 contains an ECG port 140 in the housing 130, for plugging in an ECG cable assembly. Moreover, the ECG device 106 could have additional ports (not shown), and another component 144 for the above-described additional features, such as for receipt of patient signals and/or providing therapy to the patient. The therapy can include defibrillation or pacing, for instance.

The ECG device 106 also includes a measurement circuit 146. The measurement circuit 146 receives physiological signals from the ECG port 140, and also from other ports, if provided. These physiological signals are sensed, and information about them is rendered by the measurement circuit 146 as data, or other signals, etc.

The ECG device 106 also includes a processor 148. The processor 148 may be implemented in any number of ways. Such ways include, by way of example and not of limitation, digital and/or analog processors such as microprocessors and digital-signal processors (DSPs), controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The processor 148 may include a number of modules. One such module can be a cable detection module 150, which determines a cable type of an ECG cable assembly that is connected to the ECG port and/or how many lead wires an ECG cable assembly that is connected to the ECG port 140 includes. In some examples, the cable detection module 150 can be configured to read an identifier from a memory of the ECG cable assembly, and determine the cable type and/or corresponding number of lead wires based on the identifier. For instance, the cable detection module 150 can include a coprocessor configured to read the identifier from a one-wire electrically erasable programmable read-only memory (EE-PROM) using a 1-wire communication line.

Another such module in the processor 148 can be an ECG analysis module 152, which analyzes outputs of the measurement circuit 146 to evaluate the condition of a patient's heart. The output of the ECG analysis module 152 can be provided in the form of an onscreen report and can also be primed using a printer or transmitted to another device. The displayed, printed, or transmitted report can include waveform representations of ECG signals used for the analysis, and interpretive statements of the condition of the heart or other statements concerning, for example but not limited to, ECG signal quality or analysis of additional physiological parameters.

The processor 148 can also include additional modules, such as module 158, for other functions. For instance, the processor 148 can include an ECG artifact detector. The ECG artifact detector can include a culprit electrode algorithm residing in a memory unit (not shown) in ECG artifact detector for instructing the processor 148 to implement decision rules, etc. Alternatively, the culprit electrode algorithm may reside in part or in whole on a memory 154 of the ECG device 106. The instruction to the processor 148 can be an indication of which electrodes are sensing artifact, and so on. If one or more electrodes are sensing artifact, the processor 148 is configured to report that finding to the user via a user interface 156.

In addition, if the other component 144 is provided, it may be operated in part by the processor 148 or by another processor.

The cable detection module 150, the ECG analysis module 152, and the other module 158 (if included) may take the form of executable instructions stored in the memory 154 and executed by the processor 148 to perform the specific functions of the modules.

Thus, the ECG device 106 further includes the memory 154, which can work together with the processor 148. The memory 154 may be implemented in any number of ways. Such ways include, by way of example and not of limitation, nonvolatile memories (NVM), read-only memories (ROM), random access memories (RAM), any combination of these, etc. The memory 154, if provided, may include programs containing instructions for execution by the processor 148 or other processors that may be included in the ECG device 106. The programs provide instructions for execution by the processor 148. In addition, the memory 154 can store prompts for the user 132 and/or patient data.

The ECG device 106 may also include a power source 160. To enable portability of the ECG device 106, the power source 160 may include a battery. Such a battery can be implemented as a battery pack, which can be rechargeable or not. Sometimes, a combination of rechargeable and non-rechargeable battery packs is used. Other examples of the power source 160 can include an AC power override, whereby AC power, instead of power from the power source 160, is delivered to an energy storage module 162 when AC power is available. In some examples, the power source 160 is controlled by the processor 148.

The ECG device 106 further includes the user interface 156 for the user 132. The user interface 156 can be made in any number of ways. For example, the user interface 156 may include a screen (e.g., a touchscreen) to display a parameter of a patient that is detected and measured, provide visual feedback to the rescuer for their patient care, and so on. The user interface 156 may also include a speaker, to issue voice prompts, etc. The user interface 156 may additionally include various controls, such as pushbuttons, keyboards, and so on. In addition, the discharge circuit 166 can be controlled by the processor 148, or directly by the user 132 via the user interface 156, and so on.

The ECG device 106 can optionally include other components. For example, a communication module 170 may be provided for communicating with other devices. Such communication can be performed wirelessly, or via wire, or by infrared communication, and so on. In this way, data can be communicated from the ECG device 106 to external devices, such as patient data, incident information, therapy attempted, and so on. Thus, the communication module 170 may include a receiver, transmitter, or other hardware to enable communication with the ECG device 106.

The ECG device 106 can implement electrocardiography, which is a technique of acquiring the bioelectrical voltages generated by the heart. These bio-voltages can be detected inside the body or at the skin using the electrodes mentioned above. The signals are typically detected using electrodes placed on the body surface. The ECG voltage potential between a pair of electrodes can be acquired and recorded. The ECG voltage can also be acquired as a combination of three or more electrodes. A graphical display of these ECG voltages is known as an electrocardiogram, which is often referred to as an ECG. The ECG is useful in revealing the condition of the heart and to diagnosis heart ailments or disease.

ECG data and patterns from a heart can be defined based upon a number of factors including the number of electrodes that are placed on the human body and where those electrodes are placed. The voltage from a combination of two or more electrodes is known in the art as an ECG lead, as noted above. Each ECG lead detects the ECG voltage as a combination of two, three, or four of the ten electrodes that form the ECG lead. An orientation of those ECG leads with respect to the heart also provides a directional component to the ECG voltage detected. The ECG voltage together with its directional component form a vector and the display of vectored ECG voltages provides additional information on both magnitude and angle of certain waves in the ECG (e.g., R wave).

As noted above, a 12-lead ECG can be obtained using ten electrodes, and a 15-lead ECG can be obtained using thirteen electrodes. Accordingly, in some examples, the ECG cable assembly connected to the ECG device 106 can include ten lead wires and ten electrodes. Alternatively, in other examples, the ECG cable connected to the ECG device 106 can include thirteen lead wires and thirteen electrodes.

Figure 4:
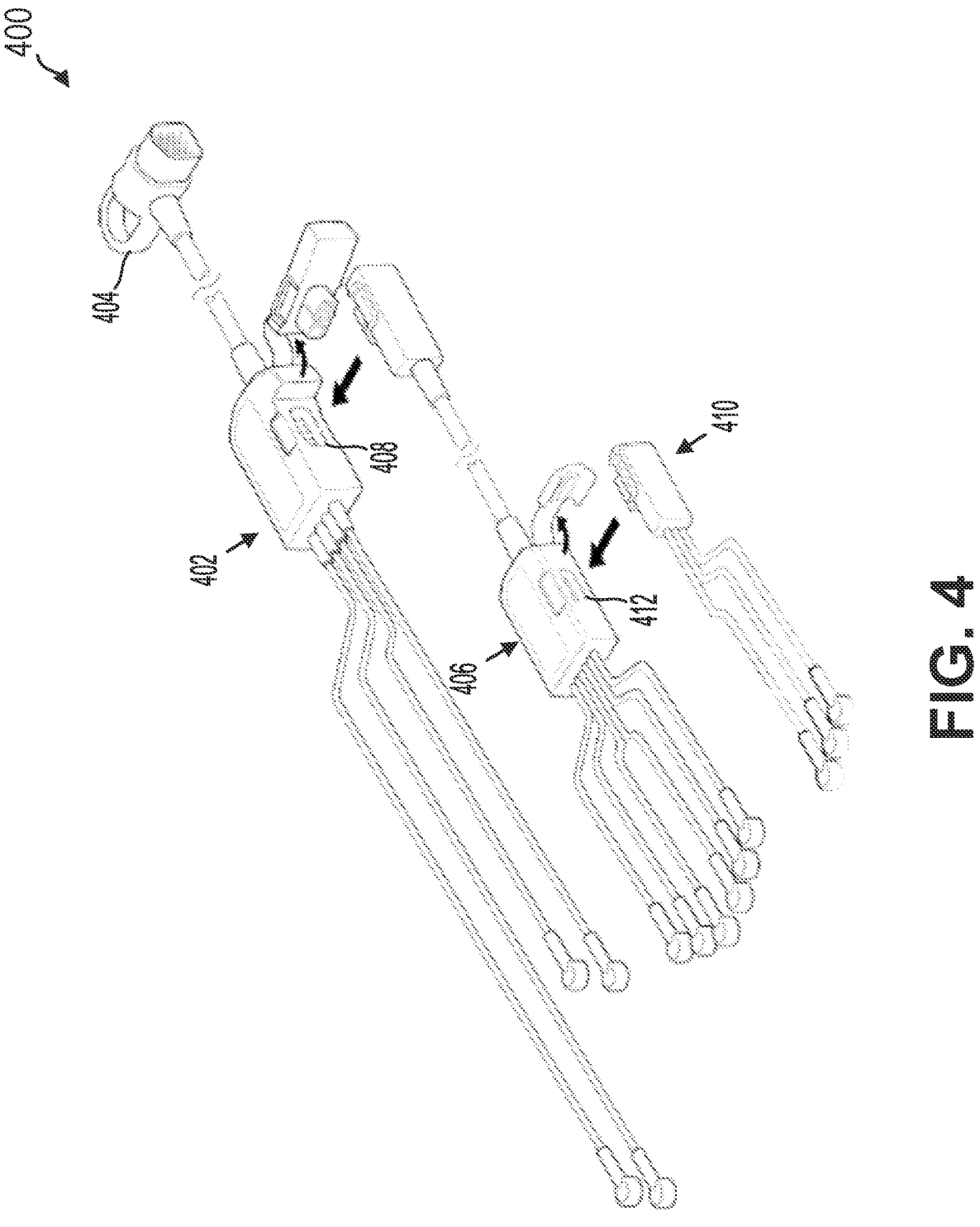
FIG. 4 illustrates an example ECG cable assembly, according to an example implementation.

FIG. 4 illustrates an example ECG cable assembly, according to an example implementation. As shown in FIG. 4, ECG cable assembly 400 includes a main trunk cable assembly 402 that provides an interface for four limb electrodes (i.e., RA, RL, LA, and LL). The main trunk cable assembly includes a connector 404 for connecting to the ECG port 140 of the ECG device 106. The main trunk cable assembly 402 can include a memory that is readable by the cable detection module 150.

In addition, the ECG cable assembly 400 includes a precordial cable assembly 406 that provides an interface for six precordial electrodes (e.g., $V_1$ to $V_6$). The precordial cable assembly 406 interfaces to the ECG device 106 through a connection to a trunk cable yoke 408 of the main trunk cable assembly. In combination, the main trunk cable assembly 402 and the precordial cable assembly 406 include ten lead wires and ten electrodes that can be used to obtain a 12-lead ECG. The precordial cable assembly 406 can include a memory that is readable by the cable detection module 150.

Further, the ECG cable assembly includes an auxiliary cable assembly 410 that provides an interface for three auxiliary electrodes (e.g., $A_1$ to $A_3$). The auxiliary cable assembly 410 interfaces to the ECG device 106 through a connection to a precordial cable assembly yolk 412. In line with the discussion above, the three auxiliary electrodes can be placed on a front, right side of the patient or on the back, left side of the patient. In combination, the main trunk cable assembly 402, the precordial cable assembly 406, and the auxiliary cable assembly 410 include thirteen lead wires and thirteen electrodes that can be used to obtain a 15-lead ECG. The auxiliary cable assembly 410 can include a memory that is readable by the cable detection module 150.

In line with discussion above, prior to forming an ECG analysis, the user interface of the ECG device 106 can provide a live-lead view such that the user can assess the quality of the electrode connections. For example, after connecting an ECG cable assembly to the ECG device 106 and attaching electrodes to the patient, a user of the ECG device 106 can select a user interface element which causes the user interface to display a live-lead view.

The live-lead view includes a representation of ECG signals. For instance, the live-lead view can include twelve waveforms corresponding to twelve ECG leads. Or the live-lead view can include fifteen waveforms corresponding to fifteen ECG leads. In some instances, the ECG device can display a placeholder for an ECG lead when the ECG lead is unavailable. For instance, if the ECG device detects that one or more electrodes used to derive the ECG lead are disconnected, the ECG device can display a dotted-line for the ECG lead or a message indicating that the ECG lead is disconnected.

In some instances, the user interface element becomes available in a navigation bar on the user interface upon connecting the ECG cable assembly to the ECG device 106. For instance, the cable detection module of the ECG cable assembly can attempt to communicate with a memory of the ECG cable assembly. Upon successfully reading an identifier from the memory, the cable detection module can determine that the ECG cable assembly is connected to the ECG device. In some examples, upon detecting that the ECG cable assembly includes at least two precordial lead wires, the ECG device can activate the user interface element that is selectable to enter the live-lead view. The cable detection module can determine the number of precordial lead wires of the ECG cable assembly based on the identifier of the ECG cable assembly.

Alternatively, in other instances, the user interface element becomes available in a navigation bar on the user interface upon connecting the ECG cable assembly to the ECG device and attaching two or more precordial electrodes to the patient. The ECG device 106 can detect a number of electrodes that are connected to the patient using the cable detection module. For instance, and attaching at least six electrodes to the patient (e.g., four limb electrodes and two or more precordial electrodes). The ECG device 106 can detect a number of electrodes that are connected to the patient using the above-referenced cable detection module. For instance, to determine whether a given electrode is connected to the patient, the cable detection module can measure an impedance between the electrode and a reference electrode using an AC or DC signal. Based on comparison of the measured impedance to one or more thresholds, the cable detection module can discern whether the electrode is connected to the patient. By repeating this process for multiple electrodes, the cable detection module can determine a number of lead wires of the ECG cable assembly.

Further, in some examples, the ECG device 106 can use the number of detected lead wires as a basis for selecting between a first live-lead view and a second live-lead view, and display the representation of the ECG signals in the selected live-lead view in accordance with the selection. For instance, the first-live lead view can be a live twelve-lead view and the second live-lead view can be a live fifteen-lead view. Upon determining that the number of lead wires is ten, the ECG device can display the live twelve-lead view. Whereas, upon determining that the number of lead wires is greater than ten, the ECG device can display the live fifteen-lead view. In some examples, upon determining that an auxiliary cable assembly is attached to a precordial cable assembly, the ECG device can determine that the number of lead wires is greater than ten. For instance, the cable detection module can read an identifier from the memory auxiliary cable assembly.

Figure 5:
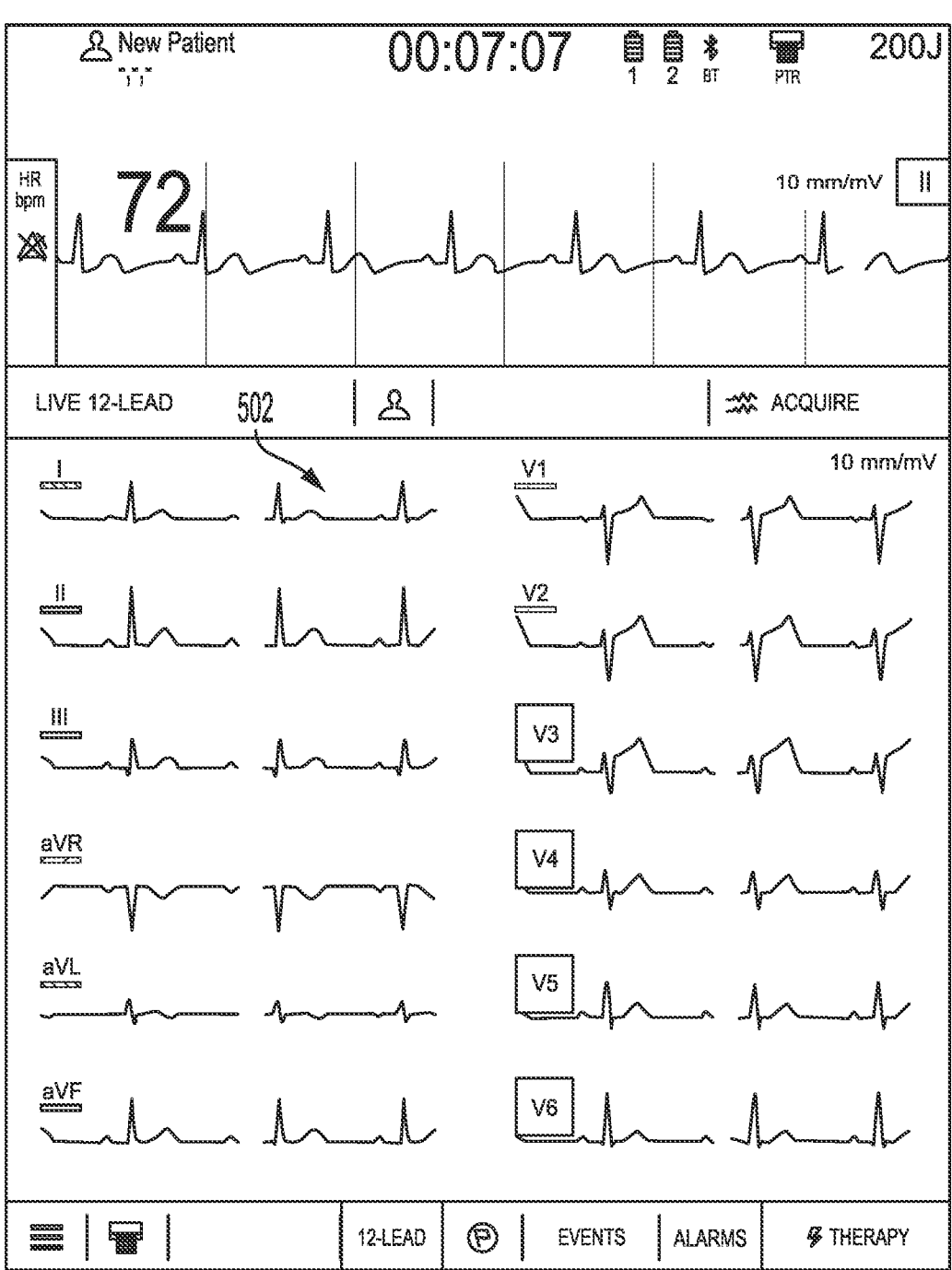
FIG. 5 illustrates an example live twelve-lead view, according to an example implementation.

FIG. 5 illustrates an example live twelve-lead view, according to an example implementation. As shown in FIG. 5, the live twelve-lead view includes waveform representations 502 for twelve different ECG leads. The waveform representations are dynamic and scroll to the left over time as the ECG device 106 obtains additional ECG data. In one example, the waveform representations may provide a near real-time view of the electrical activity of the patient's heart. For instance, the waveform representations may lag behind the electrical activity of the patient's heart by a second or two, due to the time it takes the ECG device to measure and reproduce the electrical activity on the user interface. All twelve ECG leads are visible simultaneously in two columns of six ECG leads each. In some examples, the waveform representations are displayed using a frequency response in the range of 1-30 Hz or 0.5-40 Hz or 0.05-150 Hz.

For the live twelve-lead view shown in FIG. 5, the twelve leads are labeled, by default, as I, II, II, aVR, aVL, aVF, V1, V2, V3, V4, V5, and V6. As noted above, in some instances, to obtain different perspectives of the electrical activity of a patient's heart, some of the precordial lead wires can be attached to different electrode sites. For instance, the $V_3$, $V_4$, and $V_5$ electrodes can be moved to the $V_3r$, $V_4R$, and $V_5r$ electrode sites, respectively, on the right side of the patient's chest. Alternatively, the $V_4$, $V_5$, and $V_6$ electrodes can be moved to the $V_7$, $V_8$, and $V_9$ electrode sites, respectively, on the back side of the patient's chest. To accommodate these rearrangements, labels for some of the ECG leads in the live twelve-lead view are selectable to relabel the ECG leads.

Figure 6:
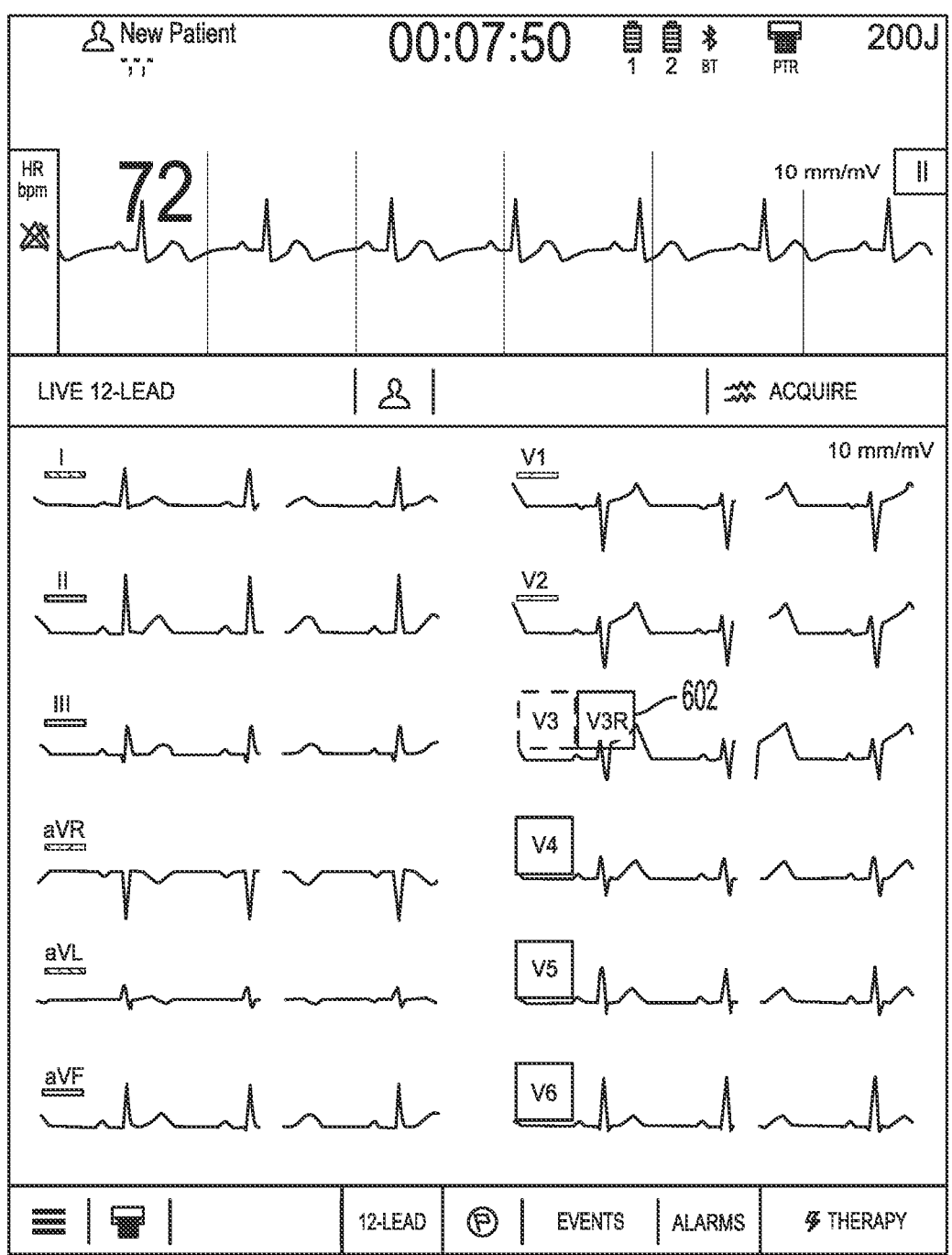
FIGS. 6-9 illustrate additional example live twelve-lead views.

FIGS. 6-9 illustrate additional example live twelve-lead views. As shown in FIG. 6, upon selecting the V3 lead (e.g., by selecting the waveform representation or the V3 label itself), the ECG device displays a menu 602 of alternate positions corresponding to the V3 lead. The menu 602 includes the V3R position. The ECG device can determine the alternate positions using correlation data that maps ECG leads to alternate positions. If the $V_3$ electrode has been attached to the $V_3R$ electrode site, a user of the ECG device can select the V3R position in the menu 602. Upon receiving a selecting of the V3R position, the ECG device then relabels the V3 lead as a V3R lead.

Figure 7:
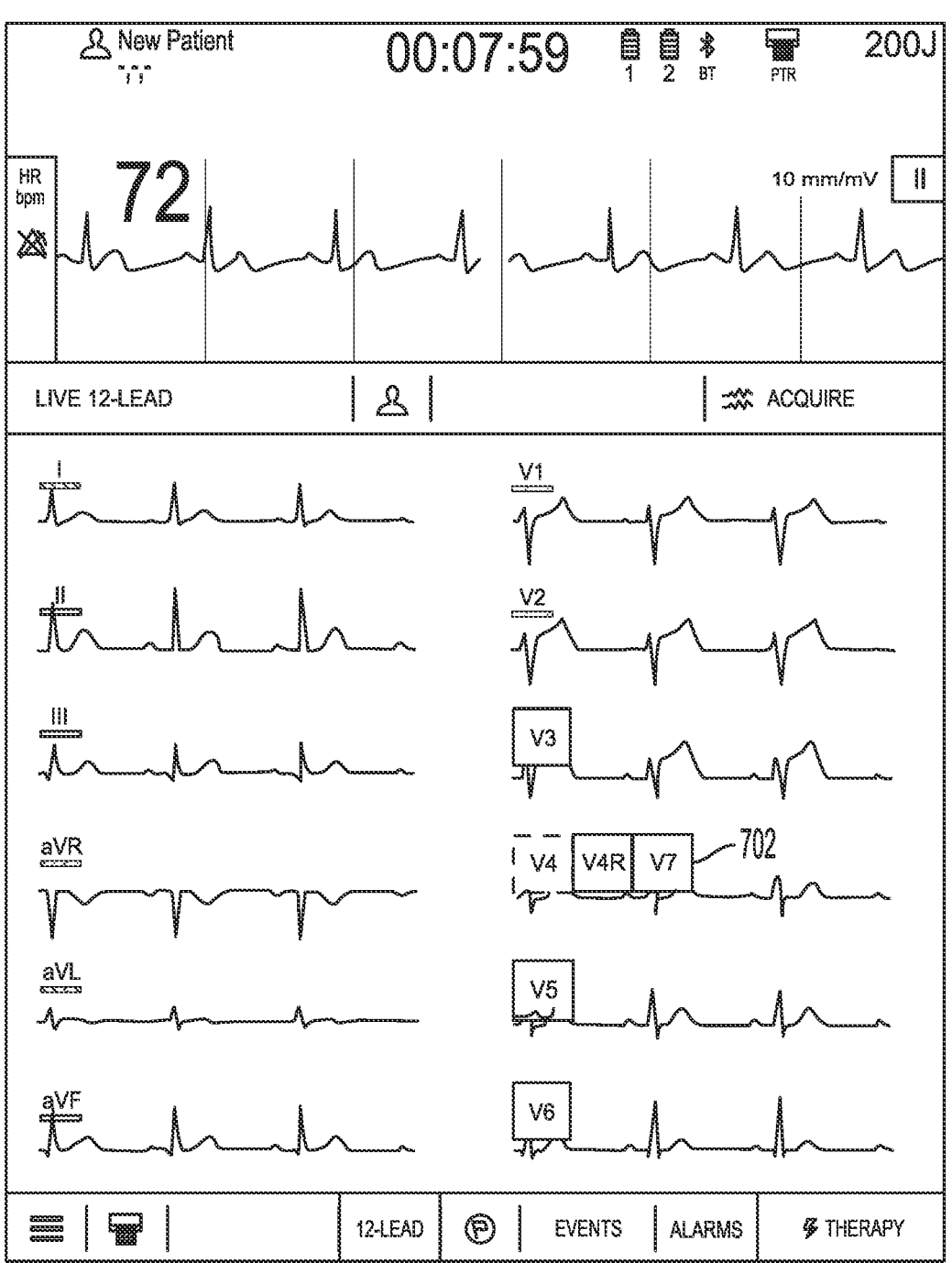

Similarly, as shown in FIG. 7, upon selecting the V4 lead, the ECG device displays a menu 702 of alternate positions corresponding to the V4 lead. The menu 702 includes the V4R position and the V7 position.

Figure 8:
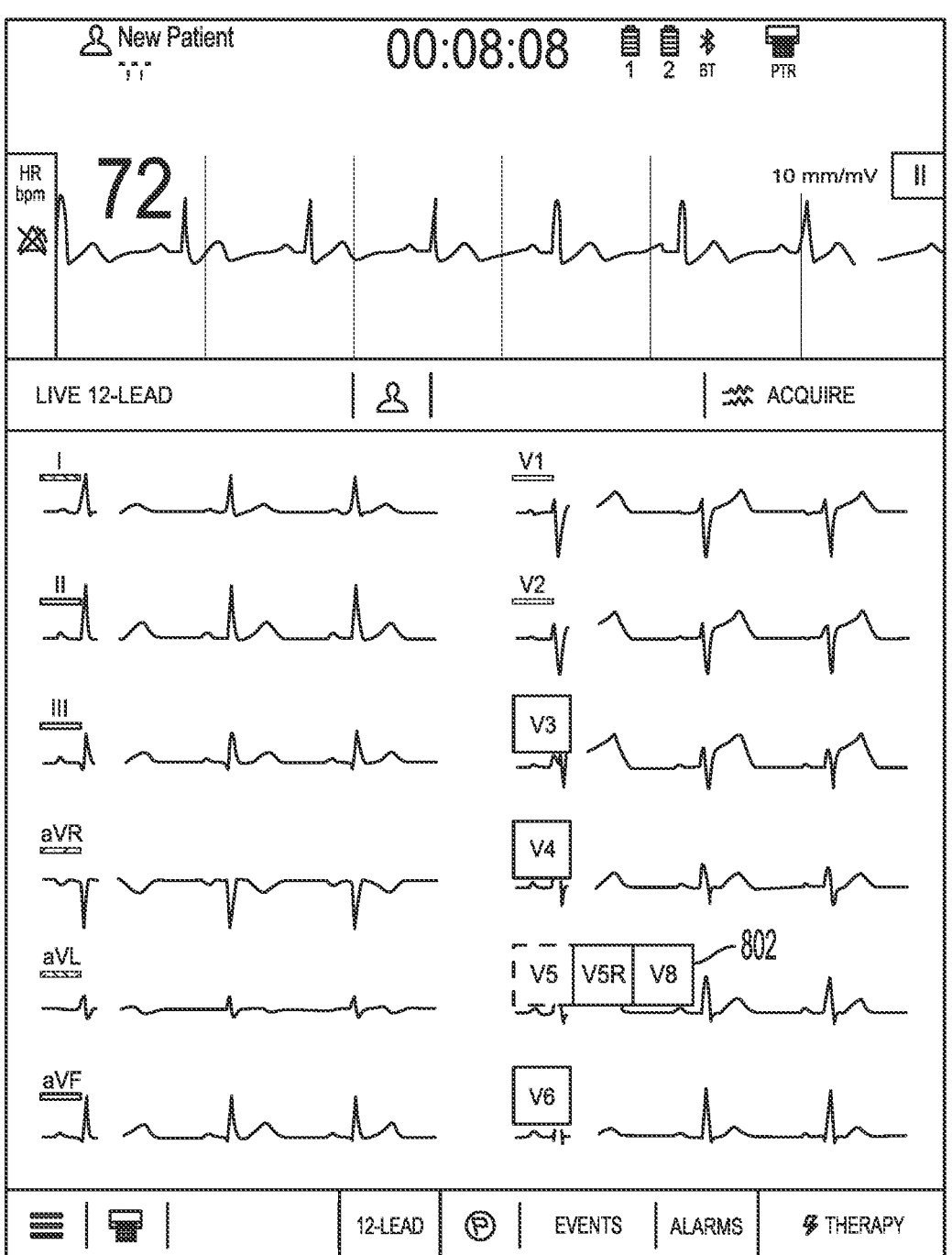

As shown in FIG. 8, upon selecting the V5 lead, the ECG device displays a menu 802 of alternate positions corresponding to the V5 lead. The menu 702 includes the V5R position and the V8 position.

Figure 9:
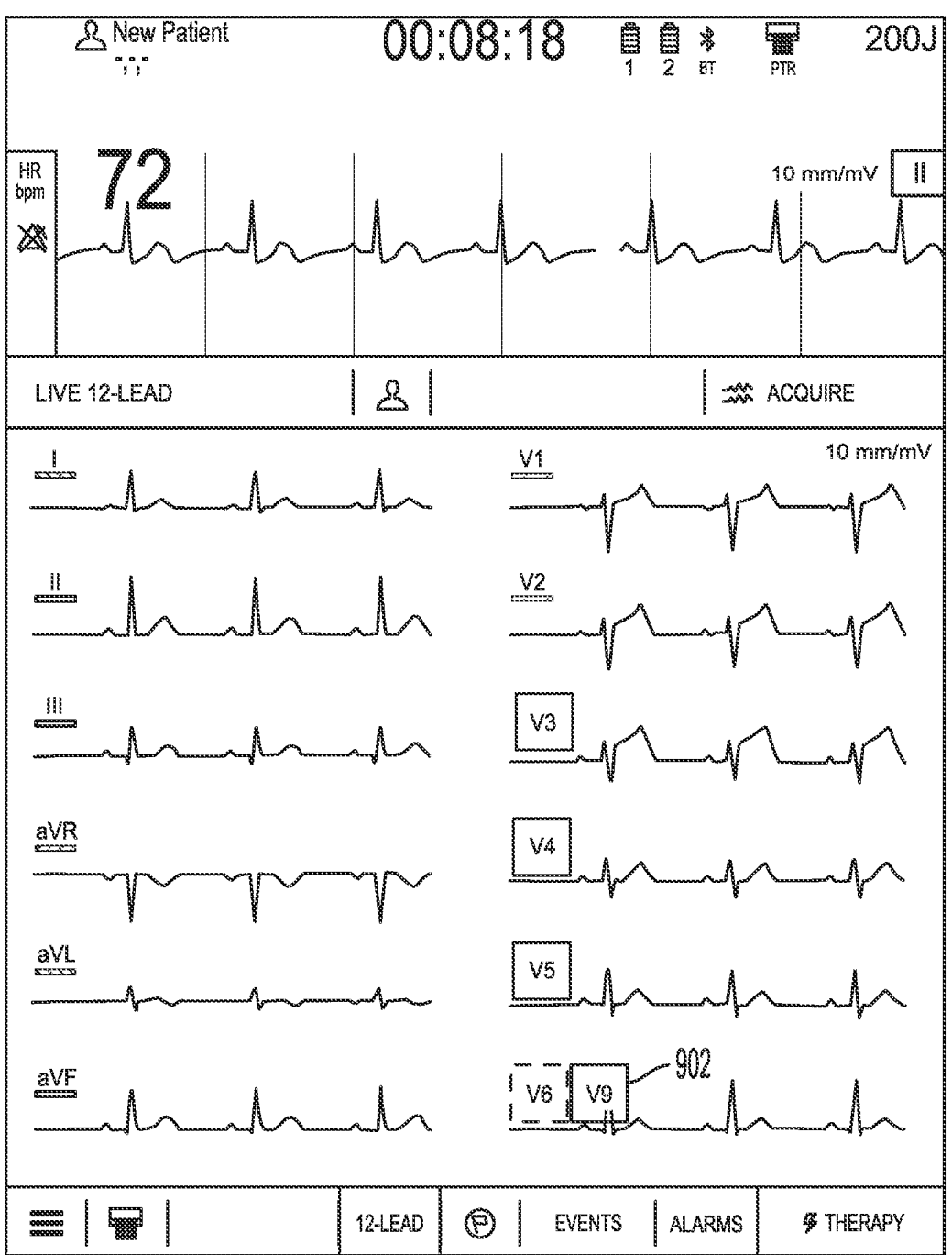

Still further, as shown in FIG. 9, upon selecting the V6 lead, the ECG device displays a menu 902 of alternate positions corresponding to the V6 lead. The menu 902 includes the V9 position.

Although the examples above describe the relabeling as involving selecting an ECG lead, in other examples, other techniques can be used to relabel an ECG lead. For instance, a user can strikethrough a label of an ECG lead on a touchscreen display of the ECG device and write in or type a new label for an ECG lead next to the label.

After relabeling any ECG leads, the ECG device can also store a record of the relabeling in memory, such that any changes to the labeling of the ECG leads can be reflected in an electronic record of the results of an analysis of the ECG signals. For instance, if an ECG lead is relabeled using the twelve-lead live view, the ECG leads will also be appropriately labeled in any subsequently generated onscreen, printed, or transmitted reports. In the past, printed ECG reports labeled ECG leads using a default manner, such as that shown in FIG. 6. If users made any changes to electrode sites for the precordial wires, the user might relabel one or more ECG leads on the printed report by crossing out a label of the ECG lead and writing in a new label. Such a manual approach is conducive to mistakes, and does not affect the electronic record of the report. Therefore, the ability to digitally store an indication of a relabeled ECG lead represents an advance over conventional approaches.

In some examples, when a user relabels an ECG lead, the ECG device can store metadata related to the change. The metadata can include a timestamp indicative of when the change occurred, a device identifier of the ECG device, and/or a user identifier of the user making the change, for instance. This metadata can be stored with an electronic record. For instance, the electronic record can include a change log that specifies related metadata for the relabeling of an ECG lead.

Further, if a report (such as any of the reports discussed herein) is generated after an ECG lead is relabeled, the report can include a visual indication of the ECG relabeling. For instance, in an ECG report, the label of the original ECG lead that was relabeled may be shown with a strikethrough, and the label of the new ECG lead can be displayed adjacent (e.g., above, below, or next to) the label with the strikethrough. For instance, when a user relabels the V6 ECG lead as a V9 ECG lead, the "V6" label can be displayed with a strikethrough and the "V9" label can be displayed to the right of the "V6".

In some examples, a user can relabel an ECG lead after an ECG report has been generated and the ECG report has been transmitted to a server device in a network for storage and/or subsequent transmittal to another computing device. For instance, the ECG device can store an archive of ECG reports. A user of the ECG device can access the ECG report within the archive of ECG reports using the ECG device or another computing device that is connected to the ECG device (e.g., via a short-range wireless communication link, via a wired communication link, or via a wireless network). The user can then relabel one or more ECG leads on the ECG report. In such a scenario, upon determining that the ECG lead(s) has been relabeled, the ECG device can transmit metadata associated with the change to a server device in a network, such that the change can be stored with an electronic record corresponding to the ECG report. In this manner, when another user reviews the electronic record, the user can readily discern that the ECG lead(s) was intentionally relabeled, and also identify information about the change, such as a timestamp and/or user identifier for the change.

Similarly, the user can use a computing device that is separate from the ECG device to access the ECG report from an electronic record that is stored by the server device. The user can then relabel one or more ECG leads on the ECG report. Further, upon determining that the ECG lead(s) has been relabeled, the computing device can transmit metadata associated with the change to a server device in a network, such that the change can be stored with an electronic record corresponding to the ECG report.

Moreover, the techniques for annotating and/or updating an electronic record with metadata indicative of changes to the electronic record are not limited to ECG devices. Rather, the techniques are also applicable to reports and electronic records related to other types of medical devices. As one example, an emergency airway management device, such as a video laryngoscope, can be used to secure a patient's airway during a patient care event. After the patient care event, the emergency airway management device can generate a report storing data related to the patient care event. After the report is generated (and optionally after the report has already been transmitted to another computing device), a user can access the report within an archive of reports stored by the emergency airway management device using the emergency airway management device or another computing device that is connected to the emergency airway management device. The user can then modify a timestamp indicating when an endotracheal tube was placed and confirmed. Based on determining that the timestamp has been changed, the emergency airway management device can transmit metadata associated with the change to a server device in a network, such that the change can be stored with an electronic record corresponding to the report.

Alternatively, the user can use a computing device that is separate from the emergency airway management device to access the report from an electronic record that is stored by a server device. The user can then modify a timestamp on the report. Further, upon determining that the timestamp on the report has been modified, the computing device can transmit metadata associated with the change to a server device in a network, such that the change can be stored with an electronic record corresponding to the report.

As another example, a cardiopulmonary resuscitation (CPR) device, such as a chest compression system or coaching device, can be used to provide patient care during a patient care event. After the patient care event, the CPR device can generate a report. After the report is generated (and optionally after the report has already been transmitted to another computing device), a user can access the report within an archive of reports stored by the CPR device using the CPR device or another computing device that is connected to the CPR device. The user can then modify a timestamp associated with the patient care event. For instance, the user can modify a placeholder timestamp to add an indication of a medication that was provided to the patient at that time. Based on determining that the timestamp has been changed, the CPR device can transmit metadata associated with the change to a server device in a network, such that the change can be stored with an electronic record corresponding to the report.

Alternatively, the user can use a computing device that is separate from the CPR device to access the report from an electronic record that is stored by a server device. The user can then modify a timestamp on the report. Further, upon determining that the timestamp on the report has been modified, the computing device can transmit metadata associated with the change to a server device in a network, such that the change can be stored with an electronic record corresponding to the report.

Figure 10:
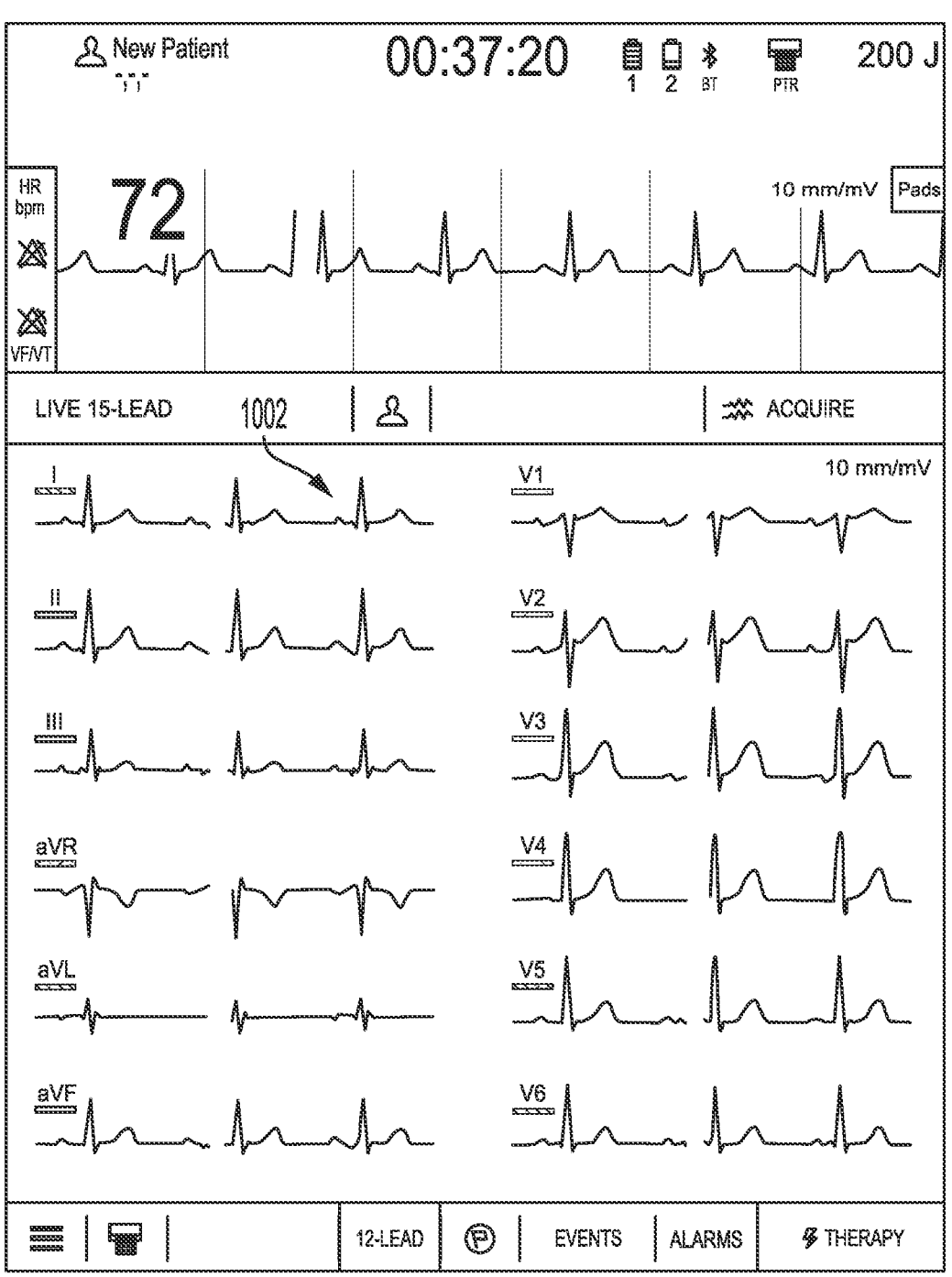
FIGS. 10 and 11 illustrate user-interface screens of an example live fifteen-lead view, according to an example implementation.
Figure 11:
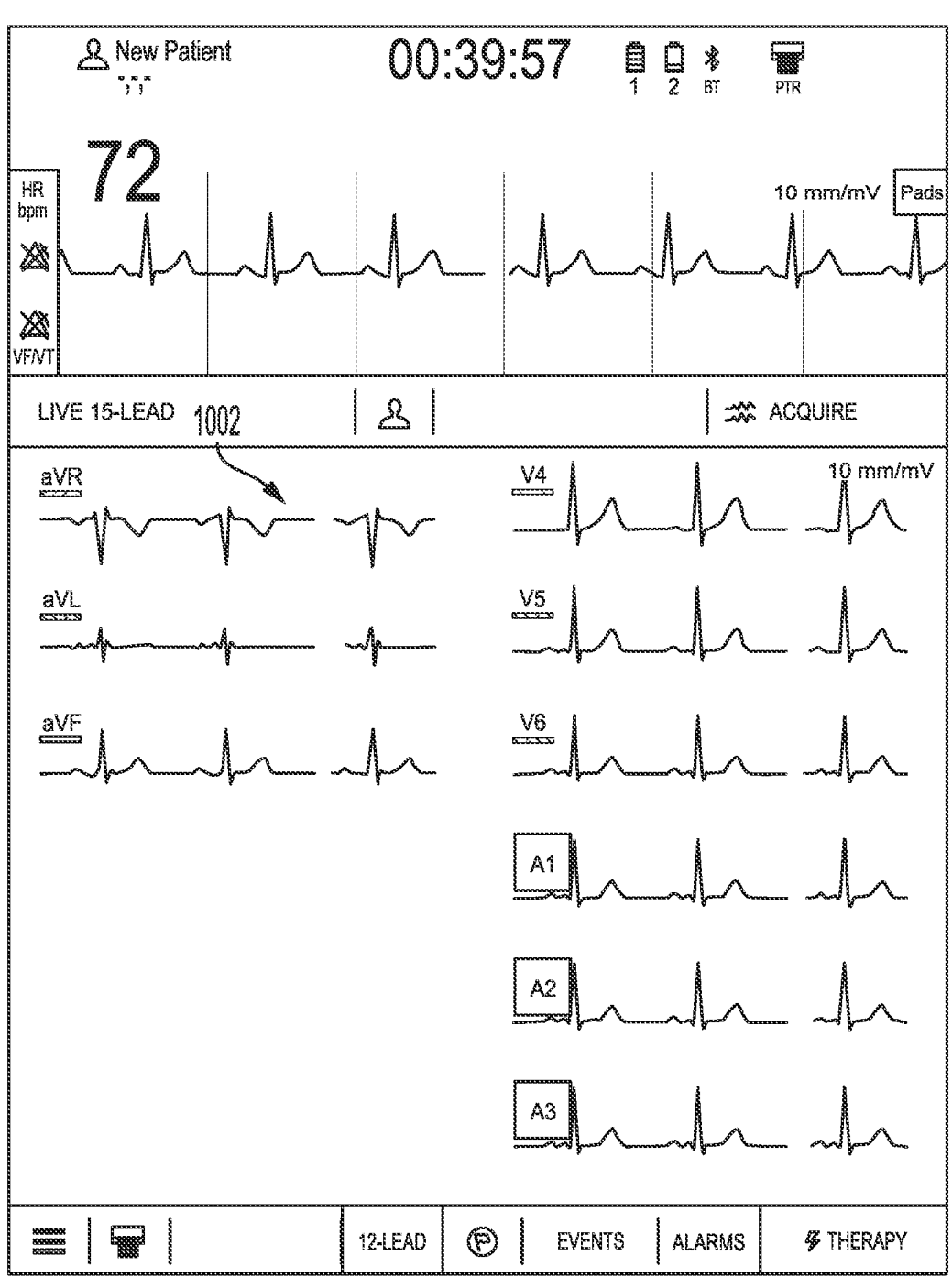

FIGS. 10 and 11 illustrate user-interface screens of an example live fifteen-lead view, according to an example implementation. As shown in FIG. 10, a first user-interface screen includes twelve ECG display positions. Within each display position a waveform representation 1002 for an ECG lead is displayed. These twelve ECG leads are labeled, by default, as I, II, II, aVR, aVL, aVF, V1, V2, V3, V4, V5, and V6.

As shown in FIG. 11, a second user-interface screen includes nine ECG display positions. Within each display position, the waveform representation 1002 for the corresponding ECG lead is displayed. These nine ECG leads include the aVR, aVL, aVF, V4, V5, and V6 leads from the first user-interface screen as well as three additional ECG leads: the A1, A2, and A3 leads.

Some ECG devices have relatively small user interfaces. Accordingly, separating the live fifteen-lead view into two user-interface screens provides an effective way to provide a live-view of fifteen different ECG leads. A user of the ECG device can switch between the first user-interface screen and the second user-interface screen using the user interface. For instance, the user interface may be a touchscreen, and the user can swipe down or select a down arrow or scroll bar to switch from the first user-interface screen to the second user-interface screen.

The first user-interface screen is visually similar to and includes the same ECG leads as the live-twelve lead view. Accordingly, in some examples, to help a user quickly discern whether the live-lead view is a live twelve-lead view or a live fifteen-lead view, the ECG device can be configured to, by default, display the second user-interface screen when the user accesses the live-lead view.

In some examples, one or more ECG leads of the live fifteen-lead view can be relabeled using the approach set forth above with reference to FIGS. 6-9. For instance, each of the A1, A2, and A3 leads can be relabeled as V3R, VR4, V5R, V7, V8, or V9.

As noted above, the live-lead view allows a user of the ECG device 106 to assess the quality of the electrode connections. In some examples, to aid the user in discerning whether the quality of the electrode connections is suitable for obtaining an ECG report, the ECG device 106 can determine whether any of the acquired ECG signals are noisy. Upon determining that one or more of the ECG signals are noisy, the ECG device 106 can generate a notification indicating that one or more of the ECG signals are noisy. In some instances, the notification can identify which ECG lead(s) are noisy and, optionally, which electrode(s) are sensing an artifact.

The ECG device 106 can determine whether any of the ECG signals are noisy using various approaches. By way of example, the ECG device 106 can analyze the ECG signals to determine whether any of the ECG signals include a threshold amount of artifact. An example method of analyzing ECG signals includes detecting an artifact in one or more of the ECG signals, classifying the artifact as a type of artifact, determining which leads contain at least a threshold amount of the type of artifact, and for the leads that contain at least the threshold amount of the type of artifact, identifying a common electrode to the leads. The ECG device then generates a notification indicating that the common electrode is sensing the artifact.

For instance, if a diagnostic 12-lead ECG is being acquired and the LL electrode has excessive artifact, the artifact will affect eleven of the twelve leads and only lead I will be unaffected. Accordingly, the ECG device can generate a notification indicating that the artifact is coming from the LL electrode. The notification may direct the user to the electrode(s) that are the source of the artifact so that they can focus their corrective action where it is needed. The ECG device can also inform the user regarding the type of artifact that is present or how to minimize the artifact that is present, to enable corrective action to take place before generating an ECG report.

The ECG device 106 can detect the artifact in the one or more of the ECG signals by digitally sampling a portion of the one or more of the ECG signals, and determining that the digitally sampled portion of the one or more of the ECG signals is outside of a range of acceptable values. The acceptable values can vary based on a number of factors. As one example, when an ECG amplitude goes above or below a range that a human ECG can nominally reach (e.g., the ECG goes outside±5 mV), an artifact is detected. As another example, when the ECG has an extremely steep slope not caused by a pacemaker stimulus, such as a slope above 1 mV/msec, an artifact is detected.

In some examples, the ECG device may display the ECG signals in the live-lead view using a first frequency response, but analyze ECG signals in the background using ECG obtained at a second frequency response having a higher bandwidth. For instance, the on-screen frequency response for the displayed ECG signals may be in the range of 1-30 Hz or 0.05-40 Hz. Whereas, the frequency response for the analyzed ECG signals may be a full diagnostic frequency response, such as 0.05-150 Hz. Conducting the noise analysis on ECG data obtained using a wider frequency bandwidth allows the ECG device to detect high frequency artifacts that might not be visually discernable from the waveform representations displayed in the live-lead view.

It is also useful to inform the user of a type of artifact that is detected. Example types of artifacts include a poor contact artifact, a motion artifact, a muscle artifact, an electromagnetic interference (EMI) artifact, and an electronic stimulator artifact.

A poor contact artifact is most commonly due to the electrode coming partially or wholly detached from the patient, but sometimes due to dried electrode gel, extremely high skin impedance, or an intermittent connection in a signal path from the electrode connector to the ECG device 106. This can cause a large amplitude artifact exceeding 3 millivolts (mV), abrupt steps in the ECG, or intermittent loss of an ECG lead. Thus, when the detected artifact has any of such characteristics, the artifact is classified as a poor contact artifact.

A motion artifact is due to patient motion of any type that can cause stretching or bending of the skin under an electrode, which can temporarily change the skin voltage by up to about 3 mV, or 30 mm at standard ECG gain. The motion may be movement by the patient, respiration, movement of the patient by a care provider (e.g., during cardiopulmonary resuscitation), or transport motion (e.g., during ambulance transport). In addition, movement of an electrostatically charged person near the patient can cause small currents to flow through the high impedance of the stratum corneum (dead skin cell layer) under an electrode, resulting in artifact voltages up to ten millivolts (100 mm) or more. Per Ohm's Law, the artifact voltage at an electrode is the current through the stratum corneum multiplied by the impedance of the stratum corneum, and the artifact voltage in an ECG lead is the combination of the artifact voltages from the electrodes that contribute to the lead, as defined in the lead equation (e.g., Equations 1 through 12 above). Motion artifact is usually low frequency artifact (a few Hz or less), but transport can cause medium frequency artifact. For example, wheel shimmy in an ambulance can cause one cycle of ECG artifact for each wheel rotation, causing artifact at a frequency of 15 Hz or more when the ambulance is moving at a typical highway speed. Motion artifact is sometimes described as a wandering baseline in the ECG, such as can occur when patient respiration stretches the skin under an electrode. Thus, when the detected artifact has any of such characteristics, the artifact is classified as a motion artifact.

A muscle artifact is commonly caused by movement by the patient or muscle tension, sometimes caused by muscle tremor. Muscle artifact appears as high frequency artifact, sometimes described as a fuzzy baseline in the ECG. Muscle artifact is also known as electromyogram (EMG) artifact. Thus, when the detected artifact has any of such characteristics, the artifact is classified as a muscle artifact.

Electromagnetic interference (EMI) artifact are most often caused by nearby line-powered equipment. The patient can act as an antenna to pick up the EMI. Most commonly, the EMI is at local line frequency, 50 or 60 Hz. Some European electric railroads have a line frequency of 16.7 Hz. Almost all electrocardiographs and ECG monitors suppress the 50 or 60 Hz line frequency, but it can still show up in the ECG if some electrodes are much closer to the source than others, or if the line-powered equipment is turning on and off as with some electric blankets. Ambulances commonly have a power inverter to convert battery voltage to AC power. Pure sine wave inverters generally do not cause problems, but modified sine wave inverters (also known as quasi-sine wave inverters or pulse width modulated inverters) by design radiate EMI at harmonics (multiples) of line frequency (e.g., 120 and/or 180 Hz if the line frequency is 60 Hz). When high frequency (e.g., 50 Hz or higher) EMI is present in the ECG, it can be seen as a thickened baseline in some ECG leads when the ECG is viewed at the full diagnostic frequency response (e.g., with the upper cutoff frequency at 150 Hz). One method for detecting EMI is to use a Fast Fourier Transform (FFT) of the ECG to view it in the frequency domain rather than the time domain. In a FFT plot, power line artifact and various other types of EMI will show up as a spike at the EMI frequency. Thus, when the detected artifact has any of such characteristics, the artifact is classified as an EMI artifact.

Electronic stimulator artifact generally include voltage spikes from stimulators such as gastric, carotid, or brain stimulators that cause unwanted artifact in the ECG. Voltage spikes from implanted pacemakers are usually considered a signal of interest, however. The artifact typically appears as a narrow spike in the ECG, sometimes often enough to cause multiple spikes per second. Spike amplitude is usually greatest in ECG leads that are largely parallel to the stimulus lead, and smallest in ECG leads that are largely orthogonal to the stimulus lead. Spikes from an electronic stimulator can be detected by looking for a rapid upslope or downslope (i.e., a fast slew rate) in the ECG. For spikes less than 5 ms wide, spike detection can be done in an ECG with a very high sample rate and a very high cutoff frequency. For example, detection of pacemaker spikes is usually done using an ECG signal with a sample rate in the range of 10 kHz to 75 kHz. False detections can be minimized by detecting only spikes within a limited range of durations. For example, almost all implanted pacemaker stimulus spikes are between 0.06 and 2 ms in duration, so spikes that are narrower or wider than that range can be excluded without degrading sensitivity for pacemaker spikes. Thus, when the detected artifact has any of such characteristics, the artifact is classified as an electronic stimulator artifact.

Additional techniques for detecting and classifying artifacts are further described in U.S. patent application Ser. No. 17/066,099 filed on Oct. 8, 2020, which is hereby incorporated by reference in its entirety.

Figure 12:
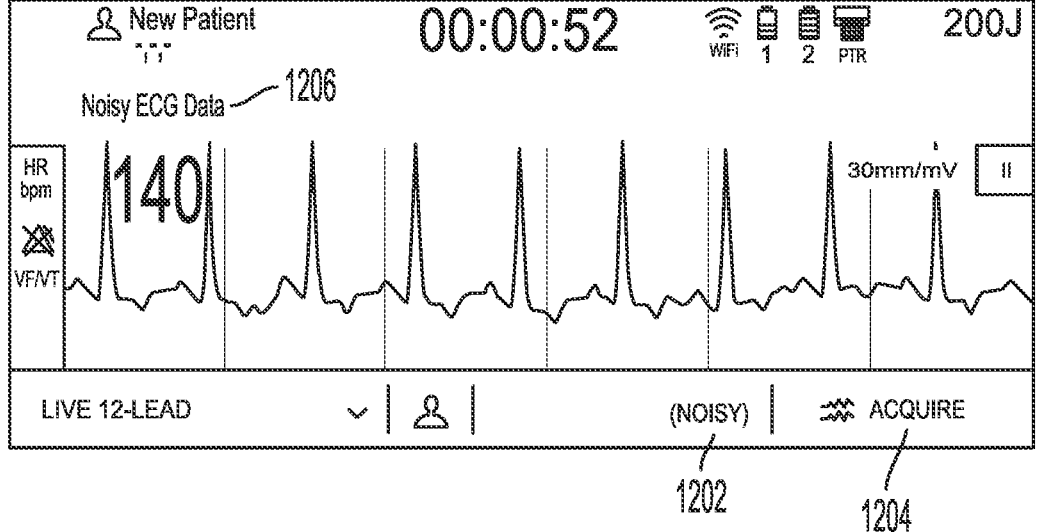
FIG. 12 illustrates an example live-lead view, according to an example implementation.

The notification generated by the ECG device 106 can be a visual notification and/or an audio notification. FIG. 12 illustrates an example live-lead view that includes multiple visual notifications, according to an example implementation. As shown in FIG. 12, upon determining that one or more of the ECG signals is noisy, the ECG device can display a noise indicator 1202 adjacent to a user interface element 1204 that is selectable to cause the ECG device 106 to acquire ECG signals, analyze the ECG signals, and generate a report.

In some examples, instead of or in addition to providing the noise indicator 1202 adjacent to the user interface element 1204, the ECG device 106 can provide a noise indicator adjacent to a waveform representation of an ECG lead that is identified as having a noisy ECG signal. Further, in addition to or instead of providing the noise indicator adjacent to an ECG lead, the ECG device 106 can modify an appearance of the waveform representation of the ECG lead or a label for the ECG lead. For instance, the ECG device 106 can change a color of the waveform representation and/or the label to a color that differs from colors of other waveform representations in the live-lead view, cause the waveform representation and/or the label to blink or animate (e.g., shrink and grow, rotate back-and-forth, etc.), or highlight a border or background of the waveform representation and/or the label.

As further shown in FIG. 12, the ECG device 106 can display a visual notification 1206 which specifies that there is noisy ECG data. In some instances, the visual notification 1206 may identify a specific ECG lead that is noisy or a specific electrode that is sensing an artifact. Further, the visual notification 1206 can specify a type of art detected by the ECG device 106. In some examples, instead of or in addition to providing the visual notification 1206 at the location shown in FIG. 12, the ECG device 106 can provide a visual notification adjacent to a waveform representation of an ECG lead that is identified as having a noisy ECG signal.

In some examples, if appropriate corrective action is not taken prior to acquiring ECG signals such that the ECG signal(s) are no longer noisy, the ECG device 106 can annotate a subsequently generated onscreen or printed report with an indication that specifies that the ECG signals are noisy, which ECG lead(s) include artifact, and/or which electrodes sensed the artifact.

Pressing or otherwise selecting the user interface element 1204 causes the ECG device 106 to acquire ECG signals for a length of time (e.g., ten seconds, twenty seconds, etc.), analyze the ECG signals, and generate an ECG report. One example of an ECG analysis algorithm is the University of Glasgow 12-Lead ECG Analysis Program. Another example of an ECG analysis algorithm is the GE-Marquette 12SL analysis program. When the ECG device 106 has finished acquiring and analyzing the ECG signals, the ECG device 106 can display an ECG report, print the ECG report, and/or transmit the ECG report to another device.

In some examples, the analysis conducted by the ECG device 106 is adjusted based on characteristics of the patient, such as age, gender, race, and/or a suspected reason/condition. If the ECG device 106 has already obtained and stored the characteristics of the patient in memory, the ECG device 106 can retrieve the characteristics from the memory. On the other hand, if the ECG device 106 has not obtained the characteristics, the ECG device can prompt the user to input the characteristics. For instance, after receiving a selection of the user interface element 1204, the ECG device can display one or more prompts. In another example, the user can access and modify the stored characteristics prior to acquiring a subsequent ECG.

Figure 13:
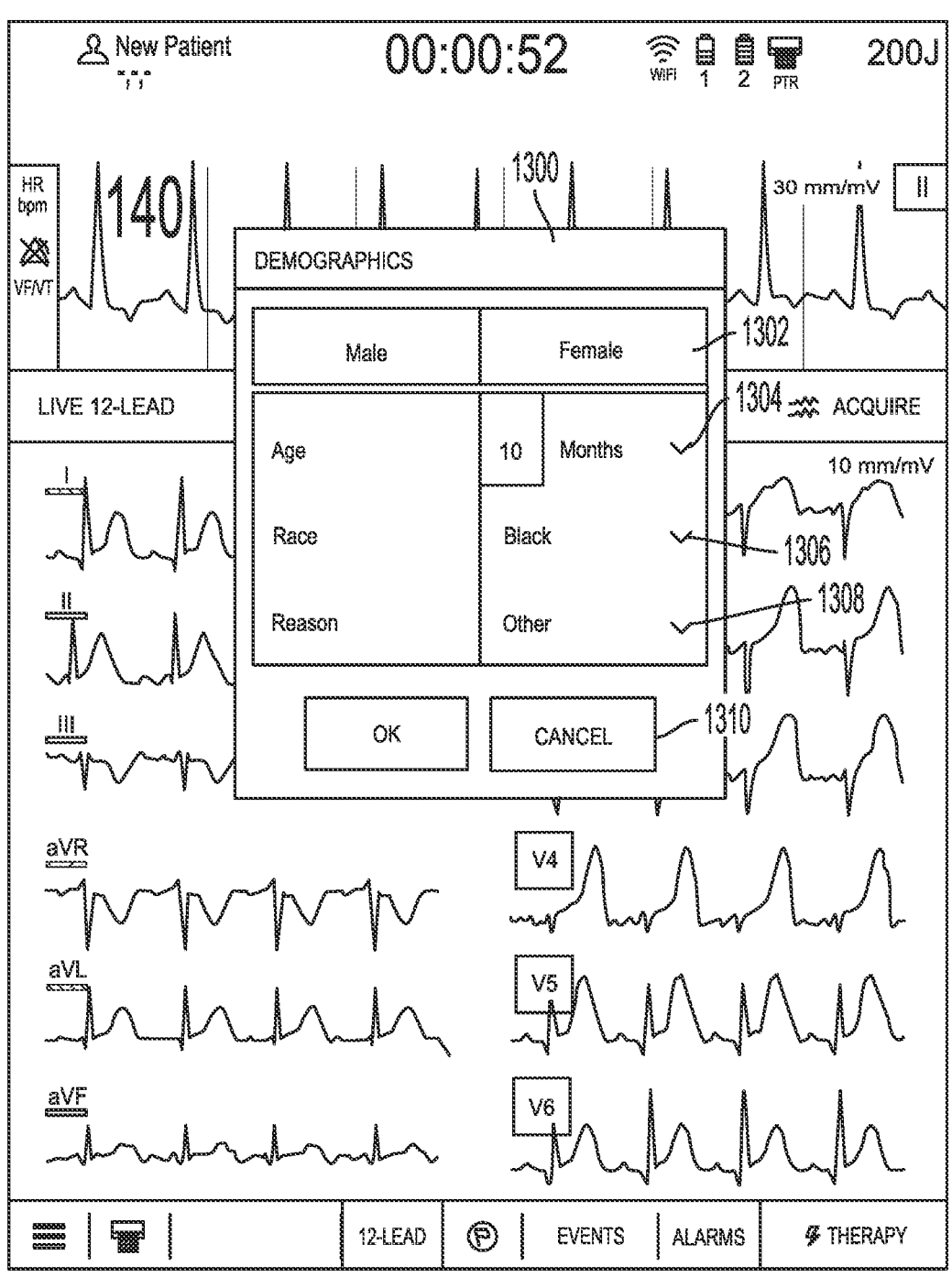
FIG. 13 illustrates an example prompt, according to an example implementation.

FIG. 13 illustrates an example prompt, according to an example implementation. As shown in FIG. 13, a prompt 1300 is displayed on top of the live-lead view. The prompt 1300 includes a gender selection element 1302, an age selection element 1304, a race selection element 1306, and a reason selection element 1308. The user of the ECG device 106 can use the gender selection element 1302, the age selection element 1304, the race selection element 1306, and the reason selection element 1308 to specify characteristics of the patient. Options for the reason selection element include: none or suspected acute coronary syndrome (ACS). If the ECG device 106 has already obtained one or more characteristics of the patient, those characters can be preselected in the prompt 1300.

If the user opts not to specify the characteristics, the user can dismiss the prompt 1300 by selecting a bypass element 1310. The ECG analysis algorithm can then be conducted using default settings defined by an ECG analysis program.

Figure 14:
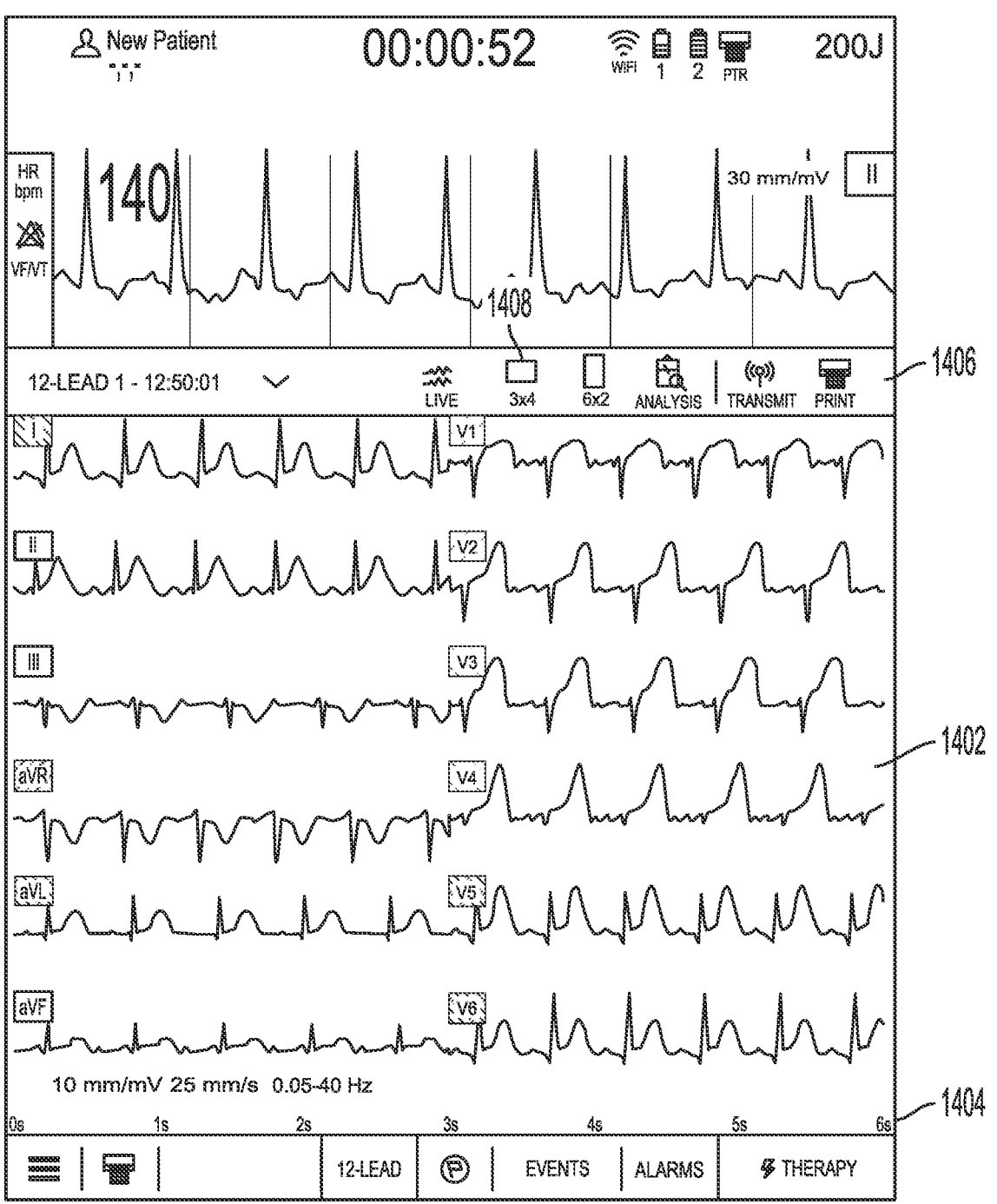
FIG. 14 illustrates an example ECG report, according to an example implementation.

FIG. 14 illustrates an example ECG report, according to an example implementation. As shown in FIG. 14, the ECG report 1402 includes waveform representations of ECG signals corresponding to the analysis time period. The waveform representations are arranged in a rectangular grid. In particular, the ECG report 1402 shown in FIG. 14 is a 12-lead ECG report, and includes twelve waveform representations arranged in two columns and six rows. For a 15-lead ECG report (not shown), fifteen waveform representations can be arranged in three columns and six rows. This format, referred to as a vertical layout, can display all ECG leads on a user interface simultaneously. In another example, the 15-lead ECG report is arranged in nine rows and two columns.

The ECG report 1402 includes a time scale 1404 to assist a user in analyzing the ECG report 1402. The user of the ECG device 106 can use navigation commands 1406 provided adjacent to the ECG report 1402 to switch back to the live-lead view, alter dimensions of the rectangular grid, view interpretative statements of the condition of the heart, transmit the ECG report 1402, or print the ECG report 1402. For instance, the user of the ECG device can select a horizontal layout element 1408 to cause the waveform representations to be rearranged into three rows and four columns, similar to how the leads appear on a one-hundred millimeter print-out.

Figure 15:
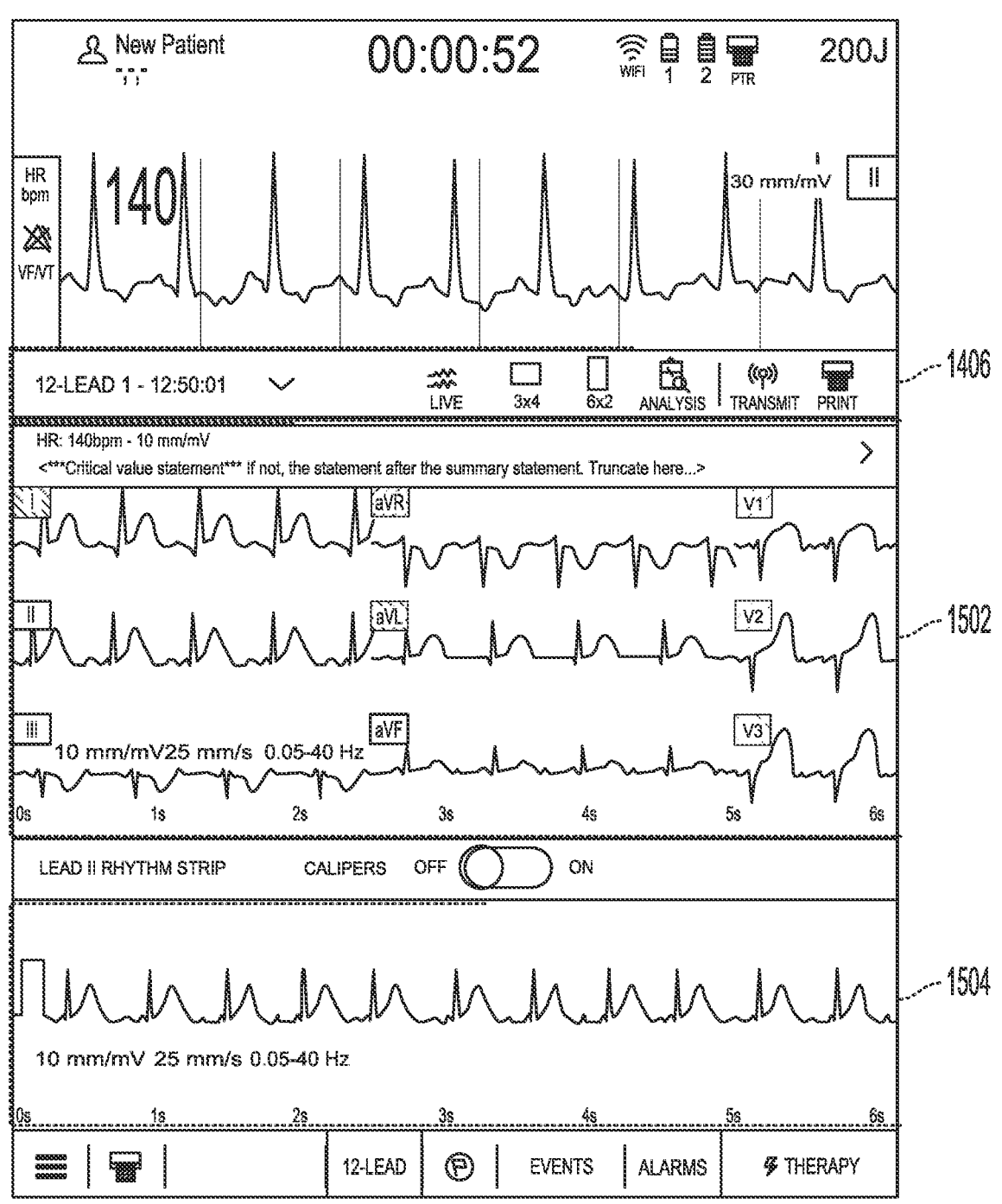
FIG. 15 illustrates another example ECG report, according to an example implementation.

FIG. 15 illustrates another example ECG report, according to an example implementation. Like the ECG report 1402 of FIG. 14, the ECG report 1502 is a 12-lead ECG report, and includes twelve waveform representations. However, the waveform representations of the ECG report 1502 are arranged in three rows and four columns, similar to how ECG leads appear on a 100-millimeter printout. For a 15-lead ECG report (not shown), fifteen waveform representations can be arranged in three rows and five columns. In this format, referred to as a horizontal layout, a user of the ECG device 106 can press and drag the ECG report 1502 to scroll to the right and view additional waveform representations. The horizontal layout can provide additional space to display an enlarged view 1504 of a waveform representation on a user interface (e.g., beneath the ECG report). A user of the ECG device 106 can alter which waveform representation is enlarged by selecting one of the waveform representations of the ECG report 1502.

FIG. 16 shows a flowchart of an example of a method 1600. Method 1600 shown in FIG. 16 presents an example of a method that could be performed by an ECG device, such as the ECG device 106 shown in FIGS. 1 and 2, for example. Further, devices or systems may be used or configured to perform logical functions presented in FIG. 16. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 1600 may include one or more operations, functions, or actions as illustrated by one or more of blocks 1602-1608. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. In this regard, each block or portions of each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long-term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block or portions of each block in FIG. 16, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

At block 1602, the method 1600 includes determining, by an ECG device, a number of lead wires of an ECG cable assembly that is attached to the ECG device. In some examples, determining the number of lead wires includes determining whether or not an auxiliary cable assembly is attached to a precordial assembly, and determining the number of lead wires based on whether or not the auxiliary cable assembly is attached to the precordial cable assembly. In some examples, determining the number of lead wires includes determining a number of electrodes that are attached to a patient.

At block 1604, the method 1600 includes receiving, by the ECG device, ECG signals using electrodes of the ECG cable assembly. Further, at block 1606, the method 1600 includes using, by the ECG device, the number of lead wires as a basis for selecting a live-lead view from among a first live-lead view and a second live-lead view. For instance, the first live-lead view can be a live twelve-lead view and the second live-lead view can be a live fifteen-lead view. With this arrangement, selecting the live-lead view can include selecting the live twelve-lead view based on the number of lead wires being ten, or selecting the live fifteen-lead view based on the number of lead wires being greater than ten.

And at block 1608, the method 1600 includes displaying, by the ECG device, a representation of the ECG signals in the selected live-lead view in accordance with the selection. For instance, the ECG device can display a live twelve-lead view or a live fifteen-lead view. The live fifteen-lead view can include a first user-interface screen including a first number of ECG display positions and a second user-interface screen including a second number of ECG display positions. With this arrangement, responsive to obtaining user input, the ECG device can switch from displaying the first user-interface screen to displaying the second user-interface screen.

In some examples, the representation of the ECG signals includes lead labels for respective ECG leads. Further, the method 1600 also includes: obtaining a selecting of an ECG lead via a user interface of the ECG device; displaying a menu of one or more alternate positions corresponding to the ECG label; obtaining a selection of an alternative position from among the one or more alternate positions; and relabeling the ECG lead in accordance with the selection of the alternate position.

In some examples, the method 1600 also includes detecting a threshold amount of artifact in an ECG signal of the ECG signals, and based on the detecting the threshold amount of artifact, generating a notification indicating that one or more of the ECG signals are noisy. Further, the notification can identify an ECG lead corresponding to the ECG signal.

In some examples, the method 1600 also includes: after displaying the representation of the ECG signals in the selected live-lead view, obtaining an instruction to generate an ECG report; analyzing ECG signals corresponding to an analysis time period; based on the analyzing, generating an onscreen report; and displaying the onscreen report. Further, the onscreen report can include waveform representations of the ECG signals corresponding to the analysis time period that are arranged in a rectangular grid. Responsive to obtaining an instruction to alter dimensions of the rectangular grid, the ECG device can alter the dimensions of the rectangular grid (e.g., to switch from a horizontal layout to a vertical layout, or switch from a vertical layout to a horizontal layout).

A 12-lead or 15-lead ECG offers users significant advantages over a single-lead ECG lead. But due to the higher number of electrodes, it can be difficult for a user to quickly obtain a high quality ECG report with minimal noise. By using the systems and methods described herein, a user of an ECG device can observe and improve ECG quality before acquisition. For example, a user can identify a poor electrode connection, take an appropriate corrective action, observe results of such a correction in near real-time (e.g., within a second or two), and then proceed to obtain an ECG report.

Further, the systems and methods described herein provide a technique for relabeling ECG leads on the ECG device, such that correct labels are associated with ECG leads in an electronic record.

By the term "substantially" and "about" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination or any sub-combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A method comprising:
determining, by an electrocardiogram (ECG) device comprising a defibrillator monitor, a number of lead wires of an ECG cable assembly that is attached to the ECG device, wherein determining the number of lead wires comprises electrically detecting, via a continuity check between pins of the ECG cable assembly, whether an auxiliary cable assembly is attached to a precordial cable assembly of the ECG cable assembly to configure the ECG device for multi-lead ECG signal acquisition;

receiving, by the ECG device, ECG signals using electrodes of the ECG cable assembly;
using, by the ECG device, the number of lead wires being either equal to ten or greater than ten as a basis for selecting a live-lead view from among a live twelve-lead view and a live fifteen-lead view,
selecting the live twelve-lead view based on the number of lead wires being ten and selecting the live fifteen-lead view based on the number of lead wires being greater than ten, wherein a selection configures a graphical user interface of the ECG device to display a number of representations of the ECG signals equal to a number of ECG leads in the selected live-lead view based on the detected cable configuration, thereby enabling observation and adjustment of electrode connections for diagnostic quality without user input on the cable configuration; and
displaying, by the ECG device, the representations of the ECG signals in the selected live-lead view in accordance with the selection.

2. The method of claim 1, wherein:
the live fifteen-lead view includes a first user-interface screen including a first number of ECG display positions and a second user-interface screen including a second number of ECG display positions, and
the method further comprises:
obtaining user input via a user interface of the ECG device, and
responsive to obtaining the user input, switching from displaying the first user-interface screen to displaying the second user-interface screen.

3. The method of claim 1, wherein the representations of the ECG signals includes lead labels for respective ECG leads, and wherein the method further comprises:
obtaining a selection of an ECG lead via a user interface of the ECG device;
displaying a menu of one or more alternate positions corresponding to the ECG lead;
obtaining a selection of an alternative position from among the one or more alternate positions; and
relabeling the ECG lead in accordance with the selection of the alternative position.

4. The method of claim 3, further comprising determining the alternate positions by using a predefined mapping that maps ECG leads to alternate positions.

5. The method of claim 3, wherein:
the ECG lead is a V3 lead and the one or more alternate positions comprise a V3R lead,
the ECG lead is a V4 lead and the one or more alternate positions comprise a V4R lead and a V7 lead,
the ECG lead is a V5 lead and the one or more alternate positions comprise a V5R lead and a V8 lead,
the ECG lead is a V6 lead and the one or more alternate positions comprise a V9 lead, or
the ECG lead is an A1 lead, A2 lead, or A3 lead and the one or more alternate positions comprise a V3R lead, a V4R lead, a V5R lead, a V7 lead, a V8 lead, and a V9 lead.

6. The method of claim 1, further comprising:
detecting a threshold amount of artifact in an ECG signal of the ECG signals; and
based on detecting the threshold amount of artifact, generating a notification indicating that one or more of the ECG signals are noisy.

7. The method of claim 6, wherein the notification identifies an ECG lead corresponding to the ECG signal.

8. The method of claim 1, further comprising:

after displaying the representation of the ECG signals in the selected live-lead view, obtaining an instruction to generate an ECG report;

analyzing ECG signals corresponding to an analysis time period;

based on the analyzing, generating an onscreen report; and displaying the onscreen report.

9. The method of claim 8, wherein:

the onscreen report includes waveform representations of the ECG signals corresponding to the analysis time period, the waveform representations of the ECG signals are arranged in a rectangular grid, and the method further comprises:

obtaining an instruction to alter dimensions of the rectangular grid; and responsive to obtaining the instruction, altering the dimensions of the rectangular grid such that at least one waveform representation of the waveform representations is moved to a different position within the rectangular grid.

10. The method of claim 8, further comprising:

receiving a selection of one of the waveform representations; and displaying an enlarged view of the waveform representation.

11. The method of claim 1, further comprising:

determining that a lead wire that is used to develop an ECG lead is disconnected; and providing a notification indicating that the ECG lead is unavailable.

12. A non-transitory computer-readable medium having stored therein a plurality of executable instructions, which when executed by an electrocardiogram (ECG) device comprising a defibrillator monitor causes the ECG device to perform functions comprising:

determining a number of lead wires of an ECG cable assembly that is attached to the ECG device, wherein determining the number of lead wires comprises electrically detecting, via a continuity check between pins of the ECG cable assembly, whether an auxiliary cable assembly is attached to a precordial cable assembly of the ECG cable assembly to configure the ECG device for multi-lead ECG signal acquisition;

receiving signals using electrodes of the ECG cable assembly;

using the number of lead wires being either equal to ten or greater than ten as a basis for selecting a live-lead view from among a live twelve-lead view and a live fifteen-lead view, selecting the live twelve-lead view based on the number of lead wires being ten and selecting the live fifteen-lead view based on the number of lead wires being greater than ten, wherein a selection configures a graphical user interface of the ECG device to display a number of representations of the ECG signals equal to a number of ECG leads in the selected live-lead view based on the detected cable configuration, thereby enabling observation and adjustment of electrode connections for diagnostic quality without user input on the cable configuration; and displaying the representations of the ECG signals in the selected live-lead view in accordance with the selection.

13. An electrocardiogram (ECG) device comprising:

a defibrillator monitor;

a non-transitory computer-readable medium having stored therein a plurality of executable instructions; and a processor adapted to execute the plurality of executable instructions to:

determine a number of lead wires of an ECG cable assembly that is attached to the ECG device, wherein determining the number of lead wires comprises electrically detecting, via a continuity check between pins of the ECG cable assembly, whether an auxiliary cable assembly is attached to a precordial cable assembly of the ECG cable assembly to configure the ECG device for multi-lead ECG signal acquisition, receive signals using electrodes of the ECG cable assembly, use the number of lead wires being either equal to ten or greater than ten as a basis for selecting a live-lead view from among a live twelve-lead view and a live fifteen-lead view, selecting the live twelve-lead view based on the number of lead wires being ten and selecting the live fifteen-lead view based on the number of lead wires being greater than ten, wherein a selection configures a graphical user interface of the ECG device to display a number of representations of the ECG signals equal to a number of ECG leads in the selected live-lead view based on the detected cable configuration, thereby enabling observation and adjustment of electrode connections for diagnostic quality without user input on the cable configuration, and display the representations of the ECG signals in the selected live-lead view in accordance with the selection.

14. The method of claim 1, wherein the representations of the ECG signals includes waveform representations of multiple ECG leads, and wherein the method further comprises determining that a waveform representation of a particular ECG lead is indicative of poor contact between an electrode and a patient.

15. The method of claim 14, further comprising prompting the user to remove and reapply or replace the electrode or encourage the patient to hold still.

16. The method of claim 1, wherein the representation of the ECG signals is updated to reflect an improvement in quality after a corrective action to the electrode connections.

17. The method of claim 1, wherein the ECG device comprises multiple storage partitions and processors, and wherein at least one processor of the processors receives inputs from the multi-lead ECG system and processes the inputs to generate outputs stored in the memory.

\* \* \* \* \*